(12) United States Patent
Palepu et al.

(10) Patent No.: US 7,803,762 B1
(45) Date of Patent: *Sep. 28, 2010

(54) READY-TO-USE BIVALIRUDIN COMPOSITIONS

(75) Inventors: Nagesh Palepu, Southampton, PA (US); Rajeshwar Motheram, Dayton, NJ (US); Praful Shah, Superior, CO (US); Gopal Krishna, Randolph, NJ (US)

(73) Assignees: The Medicines Company, Parsippany, NJ (US); Eagle Pharmaceuticals, Inc., Woodcliff Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/545,036

(22) Filed: Aug. 20, 2009

(51) Int. Cl.
  *A61K 38/00* (2006.01)
(52) U.S. Cl. .......................................... 514/2
(58) Field of Classification Search ........................ None
  See application file for complete search history.

(56) References Cited

U.S. PATENT DOCUMENTS

| | | | |
|---|---|---|---|
| 5,196,404 | A | 3/1993 | Maraganore et al. |
| 5,240,913 | A | 8/1993 | Maraganore et al. |
| 5,268,296 | A | 12/1993 | Maschler et al. |
| 5,425,936 | A | 6/1995 | Maraganore et al. |
| 5,433,940 | A | 7/1995 | Maraganore et al. |
| 5,661,001 | A | 8/1997 | Grossenbacher et al. |
| 5,691,311 | A | 11/1997 | Maraganore et al. |
| 6,274,553 | B1 | 8/2001 | Furuya et al. |
| 2005/0153873 | A1 | 7/2005 | Chan et al. |
| 2005/0250704 | A1 | 11/2005 | Bassarab et al. |
| 2007/0093423 | A1 | 4/2007 | Tovi et al. |
| 2009/0062511 | A1 | 3/2009 | Palle et al. |
| 2009/0269422 | A1 | 10/2009 | Yu |

FOREIGN PATENT DOCUMENTS

| | | |
|---|---|---|
| CN | 101244043 | 8/2008 |
| WO | 2008134601 | 11/2008 |
| WO | 20090015028 | 1/2009 |
| WO | 20090042139 | 4/2009 |
| WO | 20090086062 | 7/2009 |

OTHER PUBLICATIONS

Declaration under 37 CFR 1.131 by Nagesh Palepu filed in U.S. Appl. No. 12/563,821 on Jan. 29, 2010.*
U.S. Appl. No. 12/180,550, filed Jul. 27, 2008, Krishna et al.
U.S. Appl. No. 12/180,551, filed Jul. 27, 2008, Krishna et al.
U.S. Appl. No. 12/180,553, filed Jul. 27, 2008, Krishna et al.
U.S. Appl. No. 12/652,872, filed Jan. 6, 2010, Motheram.
U.S. Appl. No. 12/683,045, filed Jan. 6, 2010, Motheram.
M. Staples, *Pharm. Res.*, 1992, 9:10, Suppl., S79.
K.L. Amsberry et al., Compatibility and Stability of Bivalirudin in IV Admixtures, *APPS Pharm. Sci.*, 1999, 11(S1).
D. Parkins et al., The Formulation of Biopharmaceutical Products, *PSTT* vol. 3, No. 4 Apr. 2000, p. 129-37.
FDA Label for Angiomax®, Dec. 15, 2000.
L.P. Stratton et al., Controlling Deamidation Rates in a Model Peptide: Effects of Temperature, Peptide Concentration, and Additives, *J. Pharm. Sci.*, vol. 90, No. 12, Dec. 2001, p. 2141-8.
Angiomax® U.S. Prescribing Information, Dec. 6, 2005.
A. Wakankar & R.Borchardt, Formulation Considerations for Proteins Susceptible to Asparagine Deamidation and Aspartate Isomerization, *J. Pharm. Sci.*, vol. 95, No. 11, Nov. 2006, p. 2321-36.
Office Action in U.S. Appl. No. 12/683,045 dated Jun. 8, 2010.

* cited by examiner

*Primary Examiner*—Christina Bradley
(74) *Attorney, Agent, or Firm*—Frommer Lawrence & Haug LLP; Sandra Kuzmich; Russell A. Garman

(57) ABSTRACT

Ready-to-use bivalirudin compositions, methods of using the ready-to-use bivalirudin compositions, and methods of preparing the ready-to-use bivalirudin compositions. The ready-to-use bivalirudin compositions comprise bivalirudin and one or more stabilizing agents. The one or more stabilizing agents may be buffering agents having a pKa of about 2.5 to about 6.5, pH-adjusting agents, polymers, preservatives, antioxidants, sugars or polyols, or a combination thereof. The ready-to-use bivalirudin compositions may also comprise [9-10]-cycloimido bivalirudin, [11-12]-cycloimido bivalirudin, or a combination thereof. The method of using the ready-to-use bivalirudin compositions comprises administering the ready-to-use compositions to a patient in need thereof. Further, the method of preparing the ready-to-use bivalirudin compositions comprises mixing bivalirudin with one or more stabilizing agents.

53 Claims, 3 Drawing Sheets

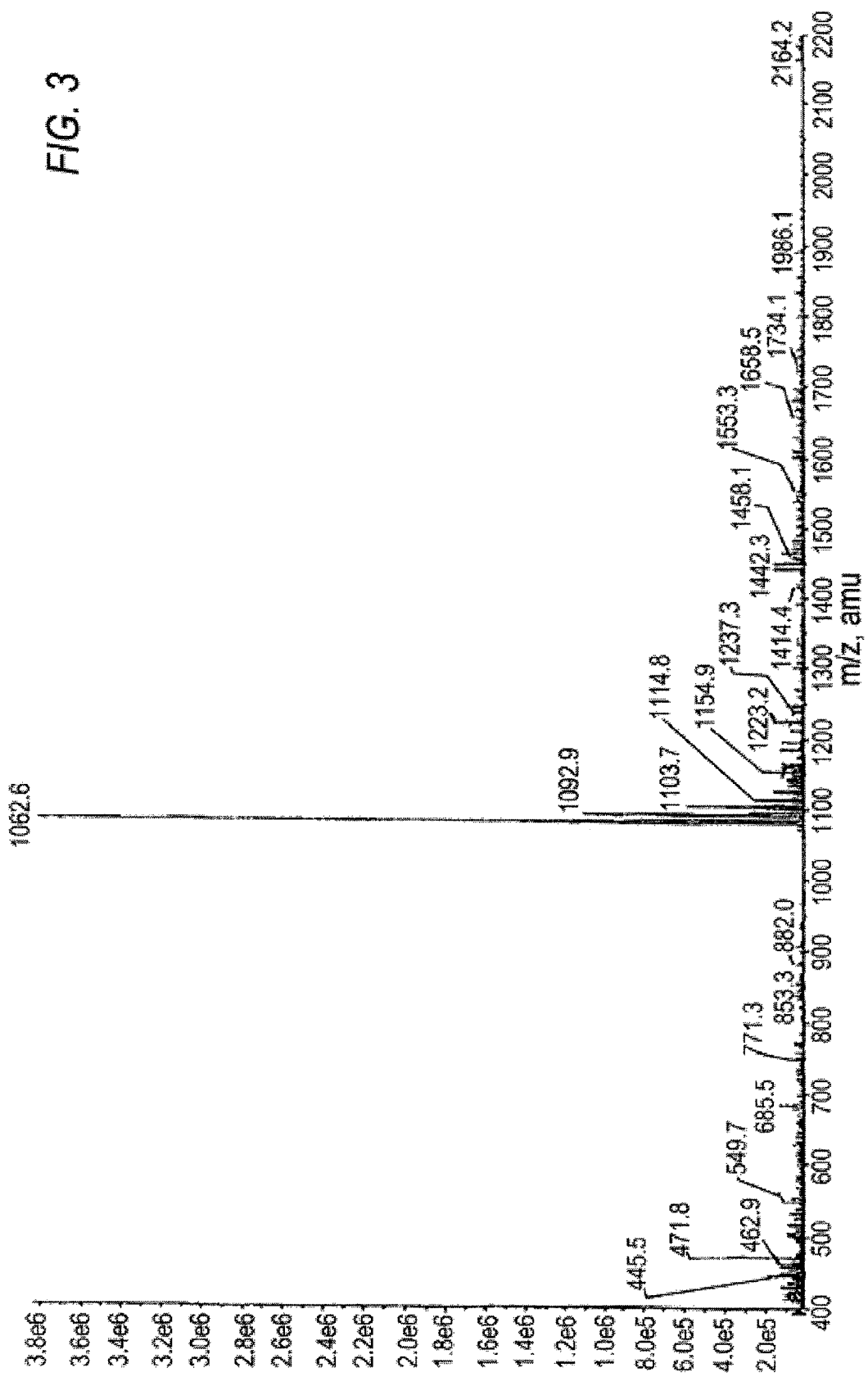

SEQUENCE LISTING

<160> NUMBER OF SEQ ID NOS: 5

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe

<400> SEQUENCE: 1

Phe Pro Arg Pro Gly Gly Gly Gly Asn Gly Asp Phe Glu Glu Ile Pro
1               5                   10                  15

Glu Glu Tyr Leu
            20

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Gly Gly Gly Gly Asn Gly Asp Phe Glu Glu Ile Pro Glu Glu Tyr
1               5                   10                  15

Leu

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe

<400> SEQUENCE: 3

Phe Pro Arg Pro Gly Gly Gly Gly Asp Gly Asp Phe Glu Glu Ile Pro
1               5                   10                  15

Glu Glu Tyr Leu
            20

```
<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe

<400> SEQUENCE: 4

Phe Pro Arg Pro Gly Gly Gly Gly Asn Gly Asp
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Glu Glu Ile Pro Glu Glu Tyr Leu
1               5
```

READY-TO-USE BIVALIRUDIN COMPOSITIONS

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention is generally directed towards stable, ready-to-use ("RTU") compositions comprising bivalirudin and one or more stabilizing agents, whereby the RTU composition has a pH of about 4 to less than 5. In certain embodiments, the one or more stabilizing agents may be buffering agents, pH-adjusting agents, polymers, preservatives, antioxidants, sugars or polyols, or a combination thereof. In some embodiments, the RTU bivalirudin compositions may comprise [9-10]-cycloimido bivalirudin, [11-12]-cycloimido bivalirudin, or a combination thereof.

The present invention is also generally directed towards a method of preparing an RTU bivalirudin composition. In various embodiments of the invention, this method may comprise mixing bivalirudin with one or more stabilizing agents to obtain an RTU composition that has a pH of about 4 to less than 5. In another embodiment of the present invention, the method may comprise mixing bivalirudin with one or more stabilizing agents and adjusting the pH to about 4 to less than 5.

Further, the present invention is generally directed towards a method of treating a patient in need thereof with the RTU bivalirudin composition. In certain embodiments, this method comprises administering the RTU bivalirudin composition to a patient in need thereof.

BACKGROUND OF THE INVENTION

Anticoagulants are substances that prevent blood from clotting. They are commonly used during percutaneous coronary intervention ("PCI") and other catherization techniques in order to reduce bleeding complications during surgery. One class of anticoagulants is direct thrombin inhibitors that disrupt the activity of thrombin, a serine protease involved in the coagulation cascade that initiates clotting when fibrinogen is converted to fibrin. Thrombin also activates Factor XIII into Factor XIIIa (the latter which links fibrin polymers covalently), Factors V and VIII (which promote thrombin generation), and platelets (which help propagate the thrombus).

Bivalirudin directly inhibits thrombin by specifically binding to both its catalytic site and anion-binding exosite, and is regarded as a highly effective anticoagulant for use during catherization procedures. Bivalirudin, also known as hirulog, is a synthetic congener of the naturally occurring thrombin peptide inhibitor hirudin, which is found in the saliva of the medicinal leech *Hirudo medicinalis*. Hirudin consists of 65 amino acids, although shorter peptide segments have proven to be effective as thrombin inhibitors. U.S. Pat. No. 5,196,404 ("'404 patent", incorporated herein by reference) discloses bivalirudin among these shorter peptides that demonstrate anticoagulant activity. However, in contrast to hirudin, bivalirudin is a reversible thrombin inhibitor that is ideal for temporary prevention of blood clotting during catherization procedures.

Bivalirudin is a synthetic 20 amino acid peptide having the chemical name of D-Phenylalanyl-L-Prolyl-L-Arginyl-L-Prolyl-Glycyl-Glycyl-Glycyl-Glycyl-L-Asparagyl-Glycyl-L-Aspartyl-L-Phenylalanyl-L-Glutamyl-L-Glutamyl-L-Isoleucyl-L-Prolyl-L-Glutamyl-L-Glutamyl-L-Tyrosyl-L-Leucine trifluoroacetate (salt) hydrate and has a molecular weight of 2180 daltons (as the free base form). Bivalirudin is made up of the amino acid sequence: (D-Phe)-Pro-Arg-Pro-Gly-Gly-Gly-Gly-Asn-Gly-Asp-Phe-Glu-Glu-Ile-Pro-Glu-Glu-Tyr-Leu (SEQ ID NO: 1). As used herein, the term bivalirudin refers to the peptide comprising SEQ ID NO: 1, and salts thereof.

Bivalirudin can be formulated into a lyophilized drug product such as Angiomax®. Approved indications for Angiomax® include treatment in patients with unstable angina undergoing percutaneous transluminal coronary angioplasty ("PTCA"); administration with the provisional use of glycoprotein IIb/IIIa inhibitor for use as an anticoagulant in patients undergoing PCI; and treatment in patients with, or at risk of, heparin-induced thrombocytopenia ("HIT") or heparin-induced thrombocytopenia and thrombosis syndrome ("HITTS") undergoing PCI. See Angiomax® Prescribing Information.

At present, bivalirudin is solely available in the form of a lyophilized composition that must be reconstituted prior to administration. In general, to administer a lyophilized drug composition, multiple steps are required as the lyophilized cake is first reconstituted, diluted and then administered. In some cases with certain drugs, the complete dissolution of the powder may require prolonged shaking. Lack of complete dissolution of certain drug powders can result in suboptimal dosing to the patient, which may result in decreased efficacy. Moreover, reconstitution introduces the potential for calculation and dilution errors. See generally Fanikos et al., *Am. J. Cardio.*, 94 (2004) 532-535.

Other drugs that are marketed as RTU products are readily available for patient administration and do not require lengthy preparation. As such, these products lead to more efficient use of hospital resources and fewer mixing mistakes and dosing errors. See generally Joint Commission, 2009 *National Patient Safety Goals Manual Chapter*; Joint Commission, Sentinel Event Alert Issue 41, Sep. 24, 2008, *Preventing Errors Relating to Commonly Used Anticoagulants*. These RTU compositions give the physicians and clinicians assurance of the appropriate drug concentration, allowing them to focus on the treatment without concern for the logistics around drug preparation. Thus, patients with cardiovascular disease, who require an immediate invasive intervention, would benefit from an RTU bivalirudin composition.

SUMMARY OF THE INVENTION

The present invention relates to an RTU bivalirudin composition comprising bivalirudin and one or more pharmaceutically acceptable stabilizing agents. In some embodiments, the composition has a pH of about 4 to less than 5. In certain embodiments, the total impurities are less than about 15% area-under-the-curve ("AUC") after storage at 25° C. for 1 month.

In embodiments of the present invention, the one or more stabilizing agents may comprise buffering agents having a pKa of about 2.5 to about 6.5, such as acetate, tartrate, ascorbate, lactobionate, gentisate, succinate, lactate, α-lipoic acid, or any combination thereof; pH-adjusting agents such as acetic acid, sodium hydroxide, or any combination thereof; polymers, such as polyethylene glycol, poloxamer, polysorbates, hydroxyethyl starch, polyvinylpyrrolidone, or any combination thereof; preservatives, such as methyl-, ethyl- and propyl-parabens or any combinations thereof; antioxidants such as histidine, methionine, or any combination thereof; or sugars or polyols, such as sucrose, dextrose, dextrin, propylene glycol, sorbitol, glycerol, or any combination thereof.

In various embodiments, the composition may further comprise one or more tonicity agents such as inorganic salts, organic salts, or a combination thereof. The inorganic salts may comprise sodium chloride, potassium chloride, magnesium chloride, or calcium chloride, and the organic salts may comprise conjugate bases of trifluoroacetic acid.

In some embodiments of the present invention, the composition may further comprise [9-10]-cycloimido bivalirudin and/or [11-12]-cycloimido bivalirudin. After storage at 25° C. for 1 month, the [9-10]-cycloimido bivalirudin may be greater than 0.2% AUC and less than about 5% AUC, and the [11-12]-cycloimido bivalirudin may be greater than 0.1% AUC and less than about 5% AUC.

In certain embodiments of the present invention, the bivalirudin is present in an amount of about 1 mg/mL to about 10 mg/mL, or about 5 mg/mL.

In embodiments of the present invention, the RTU bivalirudin composition comprises bivalirudin and one or more pharmaceutically acceptable stabilizing agents comprising a buffering agent having a pKa of about 2.5 to about 6.5; for example, the buffering agent may be acetate. The composition may further comprise a tonicity agent, such as sodium chloride. In some embodiments, the composition may additionally comprise a preservative, such as methyl-paraben. In other embodiments, the composition may additionally comprise an antioxidant such as histidine, methionine, or a combination thereof.

In certain embodiments of the present invention, the pH may be adjusted by a pH-adjusting agent.

In embodiments of the present invention, the RTU bivalirudin composition comprises bivalirudin in an amount of about 5 mg/mL; a buffering agent having a pKa of about 2.5 to about 6.5, such as acetate; [9-10]-cycloimido bivalirudin; and [11-12]-cycloimido bivalirudin. After storage at 25° C. for 1 month, total impurities may be less than about 15% AUC, and, optionally, the [9-10]-cycloimido bivalirudin may be present in an amount greater than 0.2% AUC and less than about 5% AUC, and the [11-12]-cycloimido bivalirudin may be present in an amount greater than 0.1% AUC and less than about 5% AUC. Further, the composition may have a pH of about 4.2.

In embodiments of the present invention, the RTU bivalirudin composition comprises bivalirudin in an amount of about 5 mg/mL; a buffering agent having a pKa of about 2.5 to about 6.5, such as acetate; sodium chloride; [9-10]-cycloimido bivalirudin; and [11-12]-cycloimido bivalirudin. After storage at 25° C. for 1 month, total impurities may be less than about 15% AUC, and, optionally, the [9-10]-cycloimido bivalirudin may be present in an amount greater than 0.2% AUC and less than about 5% AUC, and the [11-12]-cycloimido bivalirudin may be present in an amount greater than 0.1% AUC and less than about 5% AUC. Further, the composition may have a pH of about 4.2.

The present invention additionally relates to a method of treating a patient in need thereof with an RTU bivalirudin composition. In various embodiments, the method comprises administering an RTU bivalirudin composition comprising bivalirudin and one or more stabilizing agents. In some embodiments, the RTU bivalirudin composition is an injectable dosage form, and can be delivered to the subject parenterally. In certain embodiments, the RTU bivalirudin composition may be any of the RTU bivalirudin compositions described herein.

Furthermore, the present invention relates to a method of preparing an RTU bivalirudin composition comprising one or more stabilizing agents. In various embodiments, the method comprises mixing bivalirudin with one or more stabilizing agents. The pH of the RTU bivalirudin composition may be adjusted by one or more pH-adjusting agents to obtain a pH of about 4 to less than 5. In some embodiments, the one or more stabilizing agents may be buffering agents having a pKa of about 2.5 to about 6.5, pH-adjusting agents, polymers, preservatives, antioxidants, sugars or polyols, or a combination thereof.

These and other embodiments are disclosed or are obvious from and encompassed by, the following Detailed Description.

BRIEF DESCRIPTION OF THE FIGURES

The following Detailed Description, given by way of example, but not intended to limit the invention solely to the specific embodiments described, may best be understood in conjunction with the accompanying drawings, in which:

FIG. 3 shows the mass spectrometry results for the analysis of [11-12]-cycloimido bivalirudin.

DETAILED DESCRIPTION

Peptides containing glutamine ("Gln") and asparagine ("Asn") residues, in general, are not stable in aqueous solution and are not suitable for an RTU product due to the many mechanisms that result in degradation of the peptide in solution. These peptides commonly undergo a type of degradation reaction known as deamidation at susceptible Gln and, especially, Asn residues. Deamidation can be catalyzed at neutral and alkaline pH via a succinimide intermediate, but can also occur at acidic pH via direct hydrolysis of the side-chain amide group of the Asn residue. See Lindner et al., *Exper. Geront.* 36 (2001) 1551-1563 ("Linder et al."). Consequently, it is difficult to prevent deamidation by simple pH adjustment. See generally WO 2009086062 at 1. Degradation via deamidation is one of the reasons why most peptide-based pharmaceuticals must be produced in lyophilized (i.e., freeze-dried) form, requiring reconstitution before injection or administration. See id. at 2.

Figure 1:
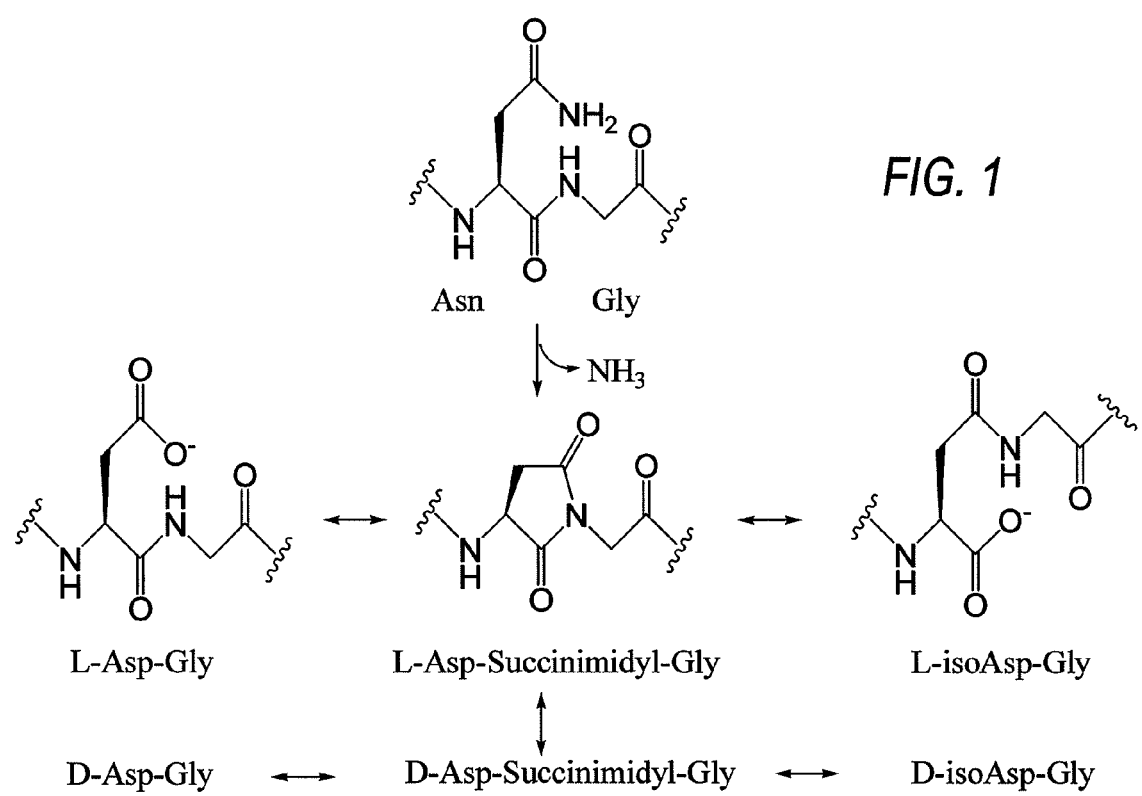
FIG. 1 shows the likely degradation pathway for the conversion of Asn-Gly residues into Asp-Gly residues.

As depicted in FIG. 1, the Asn residues of peptides and proteins, in neutral or alkaline solutions, can be deamidated via a cyclic succinimide ("cycloimido") intermediate with release of ammonia ("$NH_3$"). See Lindner et al., at 1552. The cycloimido intermediate, if it can be detected at all, is usually present in only a very small amount. See id. at 1554. Hydrolysis of this intermediate can provide the corresponding peptides containing L-aspartic acid ("L-Asp") and L-isoaspartic acid ("L-isoAsp"). See id. at 1552. Moreover, racemization of the L-Asp-cycloimido peptide can lead to formation of the corresponding D-enantiomer, and after hydrolysis can lead to peptides containing D-Asp and D-isoAsp. See id. at 1553. Bischoff et al. describes the deamidation of recombinant hirudin in neutral and alkaline environments and suggests that hirudin undergoes the same deamidation mechanism as outlined in FIG. 1. See Bischoff et al., *Biochemistry* 32 (1993) 725-734.

In acidic solutions, the mechanism of deamidation can be unpredictable since some peptides can undergo deamidation by direct hydrolysis (see id.) while other peptides can undergo deamidation by cycloimido intermediates (see Hekman et al., *J. Pharm. Biomed. Anal.*, 20 (1999) 763-772, and references therein).

Notably, some cycloimido intermediates appear to be unstable (see Lindner et al.) while others appear to be stable (see Hekman et al.); as a result, the stability of cycloimido intermediates can be unpredictable.

Bivalirudin undergoes degradation by pathways that are common to other peptides, including D-Phe-Pro cleavage (resulting in [3-20]-bivalirudin, SEQ ID NO: 2), deamidation, hydrolysis, and isomerization. Bivalirudin is susceptible to deamidation via the $Asn^9$-$Gly^{10}$ residues that can form a [9-10]-cycloimido bivalirudin intermediate (SEQ ID NO: 1, wherein $Asn^9$ and $Gly^{10}$ form a succinimide) that can then undergo hydrolysis to $Asp^9$-bivalirudin (SEQ ID NO: 3), iso$Asp^9$-bivalirudin and isomers thereof. $Asp^9$-bivalirudin is a known degradation and process impurity. See U.S. Patent Publication No. 20070093423 ("'423 publication"); U.S. application Ser. Nos. 12/180,550, 12/180,551, and 12/180,553. Controlling the formation of $Asp^9$-bivalirudin has been an ongoing challenge, although recent improvements in the preparation of Angiomax® have consistently controlled the formation of $Asp^9$-bivalirudin generated during the compounding process. See U.S. application Ser. Nos. 12/180,550; 12/180,551; and 12/180,553.

The development of RTU bivalirudin compositions of the present invention required overcoming challenges regarding the stability of bivalirudin. Notably, Angiomax® is a lyophilized powder that requires reconstitution prior to administration and has a pH of 5-6 (see Angiomax® Prescribing Information). Once reconstituted, Angiomax® may be stored at 2-8° C. for up to 24 hours. Diluted Angiomax® may have a concentration of between 0.5 mg/mL and 5 mg/mL is stable at room temperature for up to 24 hours. See id. Thus, reconstituted, or diluted, Angiomax® is not well suited for an RTU product requiring long term storage stability.

The inventors postulated that controlling $Asp^9$-bivalirudin formation would be the key challenge in developing a stable RTU bivalirudin composition. Because of the unpredictability of both the deamidation mechanism and the stability of cycloimido intermediates, the inventors conducted preliminary experiments investigating $Asp^9$-bivalirudin and total impurity levels in bivalirudin solutions at a pH range of about 2 to about 6. As described in Example 1, bivalirudin compositions were prepared and monitored at time point zero and after storage at 25° C. for 1 month. At time point zero, the inventors observed that as pH increased from about 2 to about 6 in the bivalirudin solutions, the minimum levels of $Asp^9$-bivalirudin were observed at about pH 2 and 4, and the total impurities increased as the pH increased from about 2 to about 6. After storage at 25° C. for 1 month, the bivalirudin solution at about pH 4 had the least amount of $Asp^9$-bivalirudin, although significant degradation of bivalirudin had occurred, presumably through degradation pathways other than the route depicted in FIG. 1. These results appear to suggest that a pH of about 4 may aid in the stabilization of bivalirudin solutions as initially prepared, but pH alone was not likely the controlling factor in stabilizing bivalirudin compositions for long term storage.

The inventors discovered that the $Asn^9$ residue of bivalirudin does not always directly hydrolyze to $Asp^9$ when at a pH of about 4 to less than 5 (see, e.g., Lindner et al.). Rather, the $Asn^9$-$Gly^{10}$ residues can undergo deamidation to produce the [9-10]-cycloimido bivalirudin intermediate. The inventors also discovered that the [9-10]-cycloimido bivalirudin intermediate can be detectable, can accumulate, and may be isolated under certain conditions (e.g., 2-8° C.) without further degradation to $Asp^9$-bivalirudin or isomers thereof. This can be observed in Examples 39-42 wherein $Asp^9$-bivalirudin levels (Imp. 4) increase at a slower rate than its precursor, [9-10]-cycloimido bivalirudin (as contained in Imp. 5), at 5° C. over 12 months.

The inventors discovered that maintaining the pH in a range of about 4 to less than 5 can reduce the rate of bivalirudin deamidation into [9-10]-cycloimido bivalirudin and its further degradation into $Asp^9$-bivalirudin, thereby discovering a way of controlling the level of $Asp^9$-bivalirudin in solution. However, as mentioned above, pH alone is not likely the controlling factor in stabilizing bivalirudin compositions for long term storage.

The inventors found that the concentration of other impurities increased in bivalirudin solutions upon storage. The inventors determined that these impurities were formed by an alternative degradation mechanism and must be controlled, in addition to $Asp^9$-bivalirudin, in order to achieve a stable RTU bivalirudin composition.

The inventors discovered that residues $Asp^{11}$ and phenylalanine-12 ("$Phe^{12}$") surprisingly can form a succinimide intermediate that can accumulate during storage in bivalirudin aqueous compositions at a pH of about 4 to less than 5. The formation of the intermediate would be unexpected given the large steric hindrance of the Phe residue.

Figure 2:
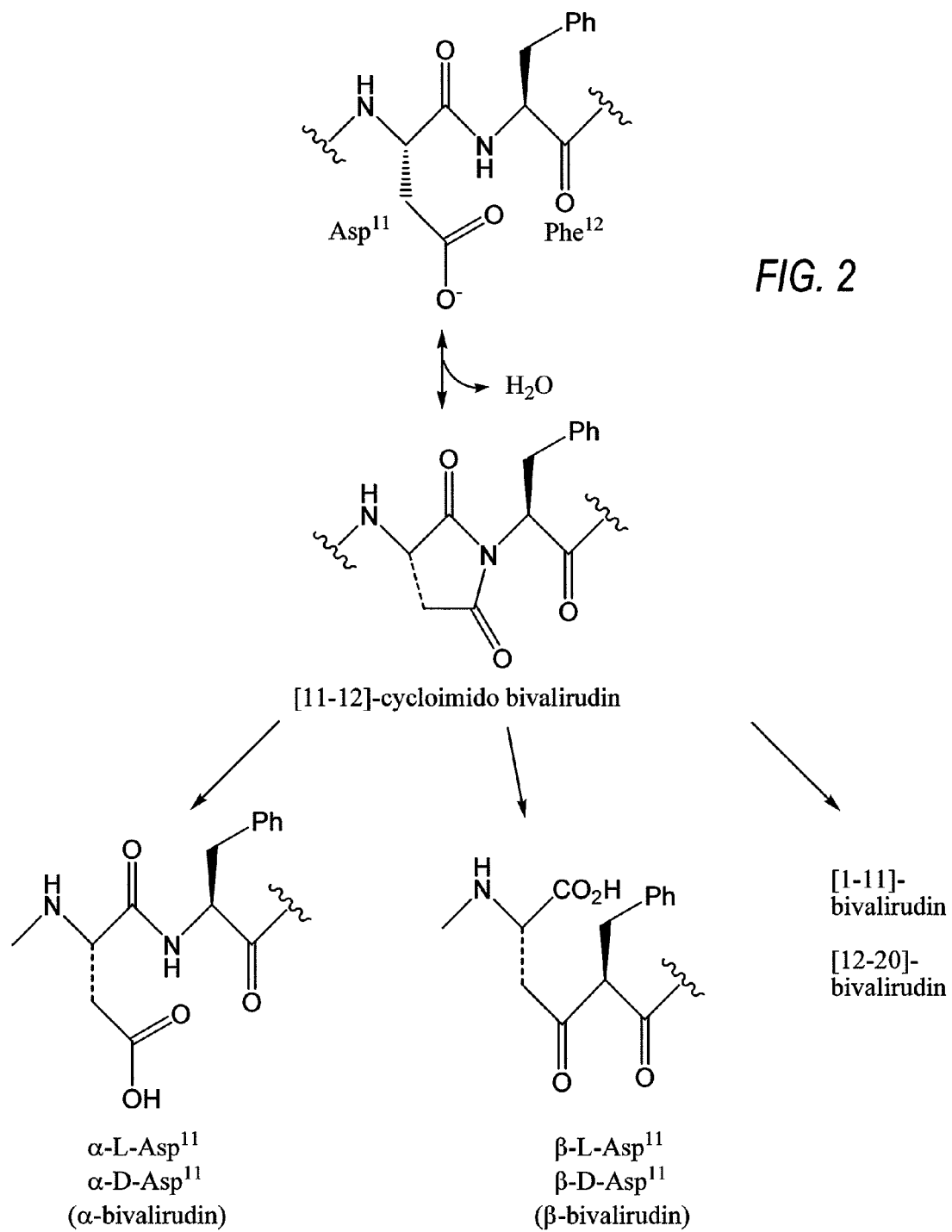
FIG. 2 shows the likely degradation pathway for the conversion of Asp-Phe residues into [11-12]-cycloimido bivalirudin.

As discovered by the inventors and shown in FIG. 2, the [11-12]-succinimide, herein called [11-12]-cycloimido bivalirudin (SEQ ID NO: 1, wherein the $Asp^{11}$ and $Phe^{12}$ form a succinimide), appears to be an intermediate of bivalirudin resulting from the cyclization of $Asp^{11}$ and $Phe^{12}$ and subsequent loss of water. The inventors characterized the [11-12]-cycloimido bivalirudin by mass spectrometry. See FIG. 3. The inventors contemplated that the [11-12]-cycloimido bivalirudin can be hydrolyzed to bivalirudin isomers and peptide fragments including the [1-11]-bivalirudin (SEQ ID NO: 4) and [12-20]-bivalirudin (SEQ ID NO: 5), and isomers thereof.

More surprisingly, the inventors found an accumulation of [11-12]-cycloimido bivalirudin (as contained in Imp. 6) in stable RTU bivalirudin compositions. Based on the bivalirudin purity in RTU bivalirudin compositions stored at 25° C. for 1 month, the inventors believe that using one or more stabilizing agents minimized the hydrolysis of the [11-12]-cycloimido bivalirudin into the impurities identified above. Thus, the stabilizing agents will likely slow down rate of formation and subsequent hydrolysis of [9-10]-cycloimido bivalirudin analogs resulting in enhanced bivalirudin stability. Likewise, the stabilizing agents will likely slow down rate of formation and subsequent hydrolysis of [11-12]-cycloimido bivalirudin analogs resulting in enhanced bivalirudin stability.

The present invention relates to an RTU bivalirudin composition comprising bivalirudin and one or more stabilizing agents. The present invention also relates to an RTU bivalirudin composition comprising bivalirudin, one or more stabilizing agents, [9-10]-cycloimido bivalirudin, and [11-12]-cycloimido bivalirudin. The present invention additionally relates to a method of treating a patient in need thereof by administering an RTU bivalirudin composition comprising bivalirudin and one or more stabilizing agents. Further, the present invention relates to a method of preparing an RTU bivalirudin composition comprising bivalirudin and one or more stabilizing agents. The present invention also relates to a method of controlling the Asp$^9$-bivalirudin levels in a solution containing bivalirudin by slowing down the rate of formation of [9-10]-cycloimido bivalirudin and its subsequent hydrolysis.

Unless defined otherwise, all technical and scientific teems used herein have the same meaning as is commonly understood by one of ordinary skill in the art to which this invention belongs. In the event that there is a plurality of definitions for a term used herein, those definitions in this section prevail unless stated otherwise.

DEFINITIONS

As used herein, a "ready-to-use" or "RTU" composition is a sterile, aqueous or non-aqueous or a combination thereof, injectable composition that is stable and has not been reconstituted from a lyophilizate within one day prior to use. The RTU composition is also a sterile, aqueous or non-aqueous or a combination thereof, injectable composition that is stable and has been diluted from a concentrated, liquid solution.

As used herein, a "sterile" composition is one in which essentially all forms of microbial life have been destroyed by an appreciable amount to meet the sterilization criteria outlined in the U.S. Pharmacopeia. See U.S. Pharmacopeia 32, NF 27, 1 (2009) 80-86.

As used herein, a "stable" composition does not exhibit appreciable degradation upon storage over a set time limit, at a set temperature, and at an identified pH. In one embodiment, no more than about 15% of bivalirudin is degraded upon storage at 25° C. over 1 month at a pH of between about 4 to less than 5. In another embodiment, no more than about 12% of bivalirudin is degraded upon storage at a temperature of about 2° C. to about 8° C. over 12 months at a pH of between about 4 to less than 5. In another embodiment, a single impurity does not exceed about 5% after storage at 25° C. for 1 month.

A "stabilizing agent" is any component that allows bivalirudin to be stable.

Various analytical techniques for measuring protein stability are available in the art and are reviewed in Lee, *Peptide and Protein Drug Delivery* (1991) 247-301, Marcel Dekker, Inc., New York, N.Y. and Jones, *Adv. Drug Delivery Rev.* 10 (1993) 29-90. Typically, a high performance liquid chromatography ("HPLC") system with appropriate hardware, software, solvents and reference standards is employed for the analysis of impurities.

As used herein, the term "has not been reconstituted from a lyophilizate" means that a solid has not been dissolved or suspended.

Bivalirudin

Bivalirudin can be synthesized by methods that include, but are not limited to, solid-phase peptide synthesis, solution-phase peptide synthesis, or a combination of solid-phase and solution-phase procedures (see, e.g., '404 patent; Okayama et al., *Chem. Pharm. Bull.*, 44 (1996) 1344-1350; Steinmetzer et al., *Eur. Biochem.*, 265 (1999) 598-605; '423 publication; U.S. Patent Publication No. 2008051558; U.S. Patent Publication No. 2008287648).

The bivalirudin in the RTU compositions may be the peptide encoded by SEQ ID NO: 1, or salts thereof. Bivalirudin may be present in an amount comprising between about 0.01 mg/mL and about 100 mg/mL, or between about 0.05 mg/mL and about 50 mg/mL, or between about 0.1 mg/mL and about 25 mg/mL, or between about 1.0 mg/mL and about 10 mg/mL, or between about 2.5 mg/mL and 7.5 mg/mL, such as a concentration of about 5.0 mg/mL.

Cycloimido-Bivalirudin and Bivalirudin Fragments

The RTU bivalirudin compositions of the present invention may comprise one or more cycloimido-bivalirudins and/or bivalirudin fragments. For example, RTU bivalirudin compositions may comprise [9-10]-cycloimido bivalirudin, [11-12]-cycloimido bivalirudin, or a combination thereof. After storage at 25° C. for 1 month, [9-10]-cycloimido bivalirudin may be greater than 0.2% AUC to less than about 5% AUC, or may be greater than about 0.5% AUC to less than about 3% AUC, while the [11-12]-cycloimido bivalirudin may be greater than 0.1% AUC to less than about 5 AUC, or may be greater than about 1% AUC to less than about 4% AUC, or may be greater than about 2% AUC to less than about 3% AUC.

Similarly, after storage at 5° C. for 12 months, [9-10]-cycloimido bivalirudin may be greater than 0.2% AUC to less than about 5 AUC, or may be greater than about 0.5% AUC to less than about 3% AUC, and the [11-12]-cycloimido bivalirudin may be greater than 0.1% AUC to less than about 5% AUC, or may be greater than about 1% AUC to less than about 4% AUC, or may be greater than about 2% AUC to less than about 3% AUC.

RTU bivalirudin compositions may also comprise one or more bivalirudin fragments, such as [3-20]-bivalirudin (SEQ ID NO: 2), [1-11]-bivalirudin (SEQ ID NO: 4), [12-20]-bivalirudin (SEQ ID NO: 5), or a combination thereof.

Stabilizing Agents

The compositions of the present invention may comprise one or more pharmaceutically acceptable stabilizing agents that include, but are not limited to, one or more buffering agents having a pKa of about 2.5 to about 6.5, pH-adjusting agents, polymers, preservatives, antioxidants, sugars or polyols, or a combination thereof. In various embodiments, the compositions further comprise a tonicity adjusting agent.

Buffering agents may comprise pharmaceutically acceptable reagents or components that contribute to maintaining the pH of bivalirudin compositions between about 4 to about less than 5. Such buffering agents may typically have pKa values that are within the target pH of the bivalirudin compositions, plus or minus about one and a half pH units. For example, buffering agents that have a pKa of about 2.5 to about 6.5 are included within the scope of the invention. Furthermore, mixed buffers wherein one buffer component falls within the pKa range of about 2.5 to about 6.5 are included within the scope of the invention. Such buffering agents that are included within the scope of the invention include, but are not limited to, ascorbate, lactobionate, gentisate, succinate, α-lipoic acid, maleate, chloroacetate, citrate, bicarbonate, tartrate, glycylglycine, formate, benzoate, citrate, lactate, acetate, propionate, pyridine, piperazine, pyrophosphate, histidine, 2-(N-morpholino)ethanesulfonic acid ("MES"), cacodylic acid, (bis(2-hydroxyethyl)-imino-tris(hydroxymethyl)-methane) ("bis-TRIS"), bicarbonate, or a combination of these buffering agents.

In one embodiment, the buffering agent may comprise a buffer having a pKa value between about 3.5 and about 5, which may include, but is not limited to, formate, benzoate, citrate, acetate, tartrate and propionate buffering agents. In particular embodiments, the buffering agent may comprise a buffer having a pKa of about 4.2 to about 4.5, such as tartrate or acetate buffering agents.

In various embodiments, the concentration of the buffering agents in the composition may be between about 0.01 M and about 10 M. In various embodiments, the buffering agent is present in a concentration of between about 0.1 M and 1 M.

The pH-adjusting agents are pharmaceutically acceptable components or reagents that are used to adjust the final pH of the RTU bivalirudin composition, the pH during the preparation of the RTU bivalirudin composition, and the pH of the buffering agent. For example, during the preparation of an RTU bivalirudin composition of the present invention, bivalirudin could be added to a buffering agent resulting in a change in the pH of the buffer solution. A pH-adjusting agent could be added to adjust the pH to the desired level during the addition of bivalirudin to the buffering agent, or after all the bivalirudin has been added. The pH-adjusting agents may include pharmaceutically acceptable acids, bases, or buffering agents. For example, the acids may include, but are not limited to, one or more inorganic mineral acids such as hydrochloric, hydrobromic, sulfuric, phosphoric, nitric, and the like; or one or more organic acids such as acetic, succinic, tartaric, ascorbic, citric, glutamic, benzoic, methanesulphonic, ethanesulfonic, trifluoroacetic and the like. The bases may be one or more inorganic bases or organic bases, including, but not limited to, alkaline carbonate, alkaline bicarbonate, alkaline earth metal carbonate, alkaline hydroxide, alkaline earth metal hydroxide or amine. For example, the inorganic or organic base may be an alkaline hydroxide such as lithium hydroxide, potassium hydroxide, cesium hydroxide, sodium hydroxide or the like; an alkaline carbonate such as calcium carbonate, sodium carbonate or the like; or an alkaline bicarbonate such as sodium bicarbonate or the like; the organic base may also be sodium acetate. Examples of buffering agents are described above.

Pharmaceutically acceptable polymers may comprise, but are not limited to, fatty esters of polyalcohols, polyalkyleneglycols and mixed polyalkyleneglycol copolymers such as poloxamer, polyethers, polyoxyethylenated fatty alcohols and esters, polysorbates ("Tween"), polyvinyl alcohols, polyalkylene oxides, polyacrylamides, polyvinylpyrrolidones, hydroxyethyl starch or combinations thereof. In certain embodiments, the polymer may be polyethyleneglycol ("PEG"). Polymers may be present in a concentration of between about 1% and about 50%, or between about 5% and about 25%, or between about 10% and about 20%.

Preservatives may comprise, but are not limited to, benzalkonium chloride, bronopol, cetrimide ("cetyltrimethylammonium bromide"), benzoic acid, benzyl alcohol, borates, chlorhexidine, chlorobutanol, nitrates, alkyl parabens including methyl- and ethyl- and propyl-paraben, phenylmercuric acetate, potassium sorbate, sodium benzoate, sorbic acid, thiomersal ("mercurithiosalicylate"), or combinations thereof. Preservatives may be present in the compositions in an amount of between about 0.01% w/w and about 5% w/w, or about 0.05% w/w and about 3% w/w, or about 0.1% w/w and about 1% w/w, or about 0.1% w/w and about 0.5% w/w, or about 0.2% w/w.

Antioxidants may comprise, but are not limited to, acetylcysteine, ascorbyl palmitate, butylated hydroxyanisole ("BHA"), butylated hydroxytoluene ("BHT"), monothioglycerol, potassium nitrate, sodium ascorbate, sodium formaldehyde sulfoxylate, sodium metabisulfite, sodium bisulfite, vitamin E or a derivative thereof, propyl gallate, edetate ("EDTA") (e.g., disodium edetate), diethylenetriaminepentaacetic acid ("DTPA"), triglycollamate ("NT"), or a combination thereof. Antioxidants may also comprise amino acids such as methionine, histidine, cysteine and those carrying a charged side chain, such as arginine, lysine, aspartic acid, and glutamic acid. Any stereoisomer (e.g., L-, D-, or a combination thereof) of any particular amino acid (e.g., methionine, histidine, arginine, lysine, isoleucine, aspartic acid, tryptophan, threonine and combinations thereof) or combinations of these stereoisomers, may be present so long as the amino acid is present either in its free base form or its salt form. For example, the L-stereoisomer is used.

In further embodiments, antioxidants can also include analogues of amino acids. The term "amino acid analogue" encompasses a derivative of the naturally occurring amino acid that brings about the desired effect of stabilizing the cycloimido bivalirudins and decreasing aggregate formation by the peptide during storage of the RTU bivalirudin compositions of the present invention. Suitable amino acid analogues include, but are not limited to, arginine analogues such as aminoguanidine, ornithine and N-monoethyl L-arginine; methionine analogues such as ethionine and buthionine; and suitable cysteine analogues such as S-methyl-L-cysteine. The amino acid analogues can be incorporated into the RTU compositions in either their free base form or their salt form.

Antioxidants may be present in the compositions in a quantity of between about 0.01% w/w and about 1% w/w, or about 0.01% w/w and about 0.5% w/w, or about 0.01% w/w and about 0.3% w/w, or about 0.01% w/w and about 0.1% w/w.

Sugars or polyols may comprise, but are not limited to, glycerin, sucrose, lactose, glucose, fructose, arabinose, xylose, ribose, mannose, galactose, dextrose, sorbose, sorbitol, mannitol, maltose, cellobiose, xylitol, or combinations thereof. The sugars or polyols may be present in the compositions in a quantity of about 1% to about 10%.

Tonicity adjusting agents, as used here, are agents that adjust the RTU bivalirudin composition to the desired isotonic range. The term "isotonic" means "isotonic with serum". An acceptable range is about 200 to about 1000 mOsm/kg. In various embodiments, the tonicity of the RTU bivalirudin composition is between about 200 to about 600 mOsm/kg. The tonicity agents that may be used in the RTU compositions may include, but are not limited to, pharmaceutically acceptable inorganic chlorides such as sodium chloride, potassium chloride, magnesium chloride, or calcium chloride; sugars such as dextrose, glycerol, lactose, sucrose, mannitol, sorbitol, and the like; or combinations thereof. Certain tonicity adjusting agents have been found to enhance the stability of RTU bivalirudin compositions containing other stabilizing agents.

The quantity of tonicity agent in the composition may vary according to the agent and according to the desired isotonic range. For example, the tonicity agent may be present in an amount between about 1 mg/mL and about 25 mg/mL, or between about 5 mg/mL and 20 mg/mL, or about 7 mg/mL and about 10 mg/mL. In certain embodiments, tonicity agent may be sodium chloride at a quantity of about 9 mg/mL, or dextrose at a quantity of about 50 mg/mL. In various embodiments, certain tonicity agents may also serve as the stabilizing agent.

RTU bivalirudin compositions of the present invention may further comprise a salt of a pH adjusting agent. During the preparation of the compositions, a pH adjusting agent may be required to obtain the target pH of the RTU bivalirudin composition. The pH adjusting agents may include pharmaceutically acceptable acids, bases, or buffering agents. Hence, the composition may include salts of any of the one or more acids, bases, or buffering agents.

Also, the pH of the final RTU bivalirudin composition of the present invention is between about 4 to less than 5. The hydrogen ion concentration is about $1 \times 10^{-4}$ M to less than about $1 \times 10^{-5}$ M.

Notably, the inventors surprisingly found that RTU bivalirudin compositions comprising different stabilizing agents, in some cases, had the same largest individual impurity at low temperature (i.e., 5° C.), while it was different at a higher temperature (i.e., 25° C.). The inventors contemplated that some stabilizing agents stabilize different degradation mechanisms at different temperatures.

Arrhenius Kinetics

Arrhenius kinetics can be used to predict the shelf life of RTU bivalirudin compositions at 5° C., according to the equation:

$$k_{obs}=Ae^{-Ea/RT}$$

wherein, $k_{obs}$ is the observed rate constant, A is the pre-exponential factor, Ea is the activation energy and R is the gas constant. According to Example 43, RTU bivalirudin compositions of Examples 32-37 and 39-40 are stable for at least 16 months of storage at 5° C.

Method of Treatment

The present invention relates to a method of treating a patient in need thereof. The method comprises administering an RTU bivalirudin composition comprising bivalirudin and one or more stabilizing agents. The RTU bivalirudin composition may be any RTU composition described herein.

The RTU bivalirudin composition can be an injectable dosage form, and can be delivered to the subject parenterally. Methods of delivering the RTU bivalirudin composition parenterally are well known in the art. For example, the aqueous composition may be delivered intravenously.

The aqueous composition may be an intravenous bolus dose of between about 0.25 mg/kg and about 1.5 mg/kg, or between about 0.5 mg/kg to about 1 mg/kg, or about 0.75 mg/kg. This may be followed by an infusion of between about 1.25 mg/kg/h and about 2.25 mg/kg/h, or about 1.75 mg/kg/h for the duration of the procedure or treatment protocol. Five minutes after the bolus dose is administered, an additional bolus of between about 0.1 mg/kg and about 1 mg/kg, or about 0.3 mg/kg, may be given if needed.

The RTU bivalirudin composition of the present invention can be indicated for use as an anticoagulant. Also, the RTU bivalirudin composition can be used for the prevention and treatment of venous thromboembolic disease. Likely indications include treatment in patients with unstable angina undergoing percutaneous transluminal coronary angioplasty; administration with the provisional use of glycoprotein IIb/IIIa inhibitor for use as an anticoagulant in patients undergoing PCI; and treatment in patients with, or at risk of, HIT or HITTS undergoing PCI. Also, RTU bivalirudin composition can be used for the prevention and treatment of venous thromboembolic disease.

The RTU bivalirudin composition may be administered with other drug products such as glycoprotein IIb/IIIa inhibitor (see, e.g., Allie et al., *Vasc. Dis. Manage.* 3 (2006) 368-375). Alternatively, RTU bivalirudin compositions may be combined with blood thinners including, but not limited to, coumadin, warfarin, and preferably, aspirin.

Method of Preparing a RTU Bivalirudin Composition

The present invention relates to a method of preparing an RTU bivalirudin composition comprising bivalirudin and one or more stabilizing agents. The method comprises mixing one or more stabilizing agents with bivalirudin to form the RTU bivalirudin composition. Optionally, the method may also comprise adjusting the pH of the RTU bivalirudin composition if the solution does not have a pH of about 4 to less than 5.

The one or more stabilizing agents may first be dissolved in water prior to mixing with bivalirudin. The stabilizing agents may comprise any of the buffering agents, pH-adjusting agents, polymers, preservatives, antioxidants, sugars or polyols, or a combination thereof, as described above.

The one or more stabilizing agents may be dissolved in water by methods known in the art. For example, the stabilizing agents may be dissolved by adding each stabilizing agent to water, by adding the stabilizing agents to each other and then mixing them with water, by mixing the one or more stabilizing agents and water in a common receptacle, or a combination thereof. The one or more stabilizing agents may be added simultaneously, individually in a particular order, individually in any order, or a combination thereof, e.g., some stabilizing agents are added together while others are added individually in a particular order. Reasons for adding stabilizing agents in a particular order may include, but are not limited to, preventing a reaction that may occur when two particular agents are mixed directly together, stimulating a reaction that may occur when two particular agents are mixed directly together, maintaining a certain pH, tonicity, etc., and ease of handling.

The one or more stabilizing agents may be dissolved in water using a mixing device that is known in the art. Examples of mixing devices may include, but are not limited to, a paddle mixer, magnetic stirrer, shaker, re-circulating pump, homogenizer, and any combination thereof. The mixing device may be applied at a mixing rate between about 10 and about 1500 rpm, and for between about 0.1 and about 120 minutes. The mixing device may be applied constantly as one or more stabilizing agents are added to water, sporadically, or a combination thereof, e.g., certain stabilizing agents may require more mixing than others.

The dissolution of the one or more stabilizing agents may occur under controlled conditions. For example, temperature may be controlled by means known in the art, such as by mixing the stabilizing agents together in a vessel inside a cooling jacket. The temperature may be set between about 1° C. and about 25° C., or between about 2° C. and about 10° C. Also, the dissolution of the one or more stabilizing agents may occur under conditions such as under nitrogen or at a particular humidity, etc.

Thereafter, the bivalirudin may be mixed with the dissolved stabilizing agents by methods known in the art. Bivalirudin may be added to the dissolved stabilizing agents rapidly, slowly, all at once, in portions, at a constant rate, at a variable rate, or a combination thereof. Alternatively, the stabilizing solution may be added to bivalirudin, or the stabilizing solution and bivalirudin may be added together into a common receptacle.

A mixing device known in the art may be used to mix bivalirudin and the dissolved stabilizing agents. Examples of mixing devices may include, but are not limited to, a paddle mixer, magnetic stirrer, shaker, re-circulating pump, homogenizer, and any combination thereof. The mixing device may be applied at a mixing rate between about 10 and about 1500 rpm, and for between about 0.1 and about 120 minutes. Whether bivalirudin is added to the dissolved stabilizing agents or vice versa, or whether they are added simultaneously into a common receptacle, the mixing device may be applied constantly, or sporadically, or a combination thereof, as the mixing proceeds.

The mixing of bivalirudin with the dissolved stabilizing agents may occur under controlled conditions. For example, temperature may be controlled by means known in the art, such as by mixing the bivalirudin and the dissolved stabilizing agents together in a vessel inside a cooling jacket. The temperature may be set between about 1° C. and about 25° C., or between about 2° C. and about 10° C. Also, the mixing of bivalirudin and the dissolved stabilizing agents may occur under conditions such as under nitrogen or at a particular humidity, etc.

The bivalirudin may already by dissolved in water when it is mixed with the dissolved stabilizing agents. On the other hand, the bivalirudin may be mixed in its solid form with the dissolved stabilizing agents.

In an alternative embodiment, bivalirudin may be mixed with one or more stabilizing agents prior to dissolution in water, simultaneously with dissolution in water, or a combination thereof. For example, solid bivalirudin and a first stabilizing agent may be mixed together and then dissolved in water, and then a second stabilizing agent may be mixed with the dissolved bivalirudin and first stabilizing agent. As another example, a first stabilizing agent may be dissolved in water and then mixed with bivalirudin (either in solid form or dissolved), and this resulting solution may be mixed with a second stabilizing agent (dissolved or in solid form). Such various orders of addition and mixing are all embodiments of the present invention. Notably, each of these mixing methods may include the use of mixing devices or particular mixing conditions as described above.

The solution comprising the dissolved bivalirudin and stabilizing agents is an RTU bivalirudin composition as described in certain embodiments of the present invention.

In certain embodiments of the present invention, a desired pH for the RTU bivalirudin composition may be about 4 to less than 5. If the pH of the RTU bivalirudin composition is not in this range after performing the method disclosed above, one or more pH-adjusting agents may be added to the RTU bivalirudin composition to achieve the desired pH.

Moreover, if a specific concentration of bivalirudin is desired in the RTU bivalirudin composition, the concentration can be adjusted, for example, by the addition of water to the RTU bivalirudin composition.

After the RTU bivalirudin composition is prepared, it may be sterilized. For instance, the aqueous composition may undergo aseptic filtration using, for example, a 0.2 μm disposable membrane filter. Also, sterilization may involve a freeze-thaw cycle to kill any residual vegetative bacteria. Techniques of sterilizing the aqueous composition are known in the art. See, e.g., Berovic, *Biotechnol. Annu. Rev.* 11 (2005) 257-79.

The RTU bivalirudin composition may be placed into a container having a sterile access port for piercing by a hypodermic injection needle, for example, an intravenous solution bag, bottle, vial, ampoule, pre-filled sterile syringe, together with instructions for administration.

Method of Controlling $Asp^9$-Bivalirudin Levels

The present invention also relates to a method of controlling the $Asp^9$-bivalirudin levels in a solution containing bivalirudin. This method may comprise mixing the solution with one or more stabilizing agents as described above, slowing down the rate of formation of [9-10]-cycloimido bivalirudin and its subsequent hydrolysis, thereby controlling $Asp^9$-bivalirudin levels and stabilizing bivalirudin.

This method can be used to control $Asp^9$-bivalirudin levels in solutions containing bivalirudin that are stored, for example, at 25° C. for one month, or at 5° C. for 12 months.

The invention will now be further described by way of the following non-limiting examples, which further illustrate the invention; such examples are not intended, nor should they be interpreted, to limit the scope of the invention.

EXAMPLES

The examples reported herein below illustrate the preferred embodiments of the present invention in greater detail but should not be construed to limit the invention in any way.

Example 1

Investigation of pH of Bivalirudin Solutions

The degradation pathway of bivalirudin was investigated by preparing aqueous solutions at 1 mg/ml of bivalirudin at pH 2, 3, 4, 5 and 6 (Table 1). Notably, the pH of a 1 mg/mL bivalirudin aqueous solution is about 2.8; thus aqueous solutions of sodium hydroxide or trifluoroacetic acid were added to adjust the pH to the desired level. At the initial time point, the inventors observed that as the pH was increased from about 2 to about 6, the total degradants also increased. After 1 month of storage at 25° C., significant potency loss was observed for all bivalirudin samples. Bivalirudin compositions exhibited better stability between pH of about 3 and about 4. The excessive degradation observed was attributed to a change in pH during storage wherein the final pH of the bivalirudin compositions was about 7.

TABLE 1

| pH | Time | $Asp^9$-Bivalirudin (% AUC) | Total Degradants (% AUC) |
|----|------|-----------------------------|--------------------------|
| 2 | Initial | 0.45 | 0.6 |
| 3 | Initial | 0.76 | 0.9 |
| 4 | Initial | 0.59 | 3.1 |
| 5 | Initial | 0.84 | 3.4 |
| 6 | Initial | 1.19 | 4.7 |
| 2 | 25° C./1 month | 2.58 | 64.8 |
| 3 | 25° C./1 month | 2.71 | 37.7 |
| 4 | 25° C./1 month | 1.26 | 51.1 |
| 5 | 25° C./1 month | complete degradation | |
| 6 | 25° C./1 month | complete degradation | |

Example 2

Investigation of Various Buffering Agents Added to Bivalirudin Solutions

Various buffering agents were investigated to stabilize the pH of the bivalirudin aqueous solutions. Buffered solutions of bivalirudin were prepared at pH 4.0, 4.5, 5.0, and 5.5 and the stability results indicated improved stability at a pH of about 4 to less than 5.

This result was surprising as the current Angiomax® product has a pH of about 5.2 following reconstitution prior to injection. Various buffering agents are contemplated within the scope of the invention that have an adequate buffering capacity in the pH range of about pH 4 to about less than 5, and a pKa range of about 2.5 to about 6.5.

Example 3

General Procedure for the Preparation of Laboratory Scale RTU Bivalirudin Compositions A 1 M acetic acid solution was prepared by diluting 11.5 mL of acetic acid with water in a 200 mL volumetric flask. A 1 N sodium hydroxide ("NaOH") solution was prepared by dissolving 4 g of NaOH with water in a 100 mL volumetric flask. A 0.05 M sodium acetate solution was prepared by dissolving 0.68 g of sodium acetate trihydrate in 50 mL of water.

To the sodium acetate solution was optionally added stabilizing agents (e.g., 5 mL of PEG 400). The pH of the sodium acetate solution was then adjusted to between about 4 to less than 5 with the addition of 1 M acetic acid solution.

Bivalirudin (100 mg) was slowly added with stirring to 10 mL of the sodium acetate buffer solution. The pH was adjusted to between about 4 to less than 5 with the addition of the 1 N NaOH solution and water was added (q.s. to 20 mL). The solution was filtered through a 0.45 μm membrane filter into USP Type I flint glass vials, stoppered with bromobutyl stoppers and sealed with aluminum caps.

Example 4

General HPLC Method for Analysis of Laboratory Scale RTU Bivalirudin Compositions Storage stability assessment was performed on RTU bivalirudin compositions of Examples 5-20 by means of HPLC using the following experimental conditions Mobile Phase A: 0.1% TFA in water Mobile Phase B: 0.1% TFA in acetonitrile Column: Jupiter Proteo 90 A°, 4 μm Column, 2.0 mm×250 mm Pump Mode Gradient Flow Rate: 0.23 mL/min Wavelength: 215 nm Sample Cooler: 15° C.

Injection volume 5 μL

Run time: 65 minutes

Column temperature: 45° C.

Gradient Program: see TABLE 2

TABLE 2

| Time | Mobile Phase B % |
|---|---|
| 0.01 | 5 |
| 5.00 | 5 |
| 10.10 | 22 |
| 35.00 | 27 |
| 40.00 | 100 |
| 50.00 | 100 |
| 51.00 | 5 |
| 65.00 | 5 |
| 65.01 | Stop |

Following these conditions, the following impurities were observed:

TABLE 3

| No. | Name | RRT |
|---|---|---|
| Imp. 1 | [1-11]-bivalirudin | 0.55 |
| Imp. 2 | [12-20]-bivalirudin | 0.82 |
| Imp. 3 | [3-20]-bivalirudin | 0.85 |

TABLE 3-continued

| No. | Name | RRT |
|---|---|---|
| Imp. 4 | Asp$^9$-bivalirudin | 1.04 |
| Imp. 5 | Co-eluting peaks that include [9-10]-cycloimido-bivalirudin | 1.08 |
| Imp. 6 | Co-eluting peaks that include [11-12]-cycloimido-bivalirudin | 1.18 |

Depending on the RTU bivalirudin composition, the relative retention time ("RRT") values can shift by about 0.1 RRT units.

Example 5

In accordance with the general procedure of Example 3, the RTU bivalirudin composition shown in Table 4 was prepared.

TABLE 4

| Ingredients | Quantity |
|---|---|
| Bivalirudin | 10 mg/mL |
| Sodium acetate | 0.05 M |
| Sodium hydroxide 1 M | q.s. to pH 4.5 |
| Water | q.s. |

The samples were stored at 25° C. for 1 month and the stability data is presented below in Table 5.

TABLE 5

| | Known Impurities (% AUC) | | | | | | |
|---|---|---|---|---|---|---|---|
| Time | Imp. 1 | Imp. 2 | Imp. 3 | Imp. 4 | Imp. 5 | Imp. 6 | Total Degradants (% AUC) |
| Initial | 0 | 0 | 0 | 0 | 0 | 0.13 | 0.13 |
| 25° C./1 month | 0.28 | 2.17 | 0.97 | 0.51 | 1.07 | 1.24 | 7.4 |

Example 6

In accordance with the general procedure of Example 3, the RTU bivalirudin composition shown in Table 6 was prepared.

TABLE 6

| Ingredients | Quantity |
|---|---|
| Bivalirudin | 5 mg/mL |
| Sodium acetate | 0.05 M |
| PEG 400 | 5% |
| Sodium hydroxide 1 M | q.s. to pH 4 |
| Water | q.s. |

The samples were stored at 25° C. for 1 month and the stability data is presented below in Table 7.

TABLE 7

| | Known Impurities (% AUC) | | | | | | |
|---|---|---|---|---|---|---|---|
| Time | Imp. 1 | Imp. 2 | Imp. 3 | Imp. 4 | Imp. 5 | Imp. 6 | Total Degradants (% AUC) |
| Initial | 0 | 0 | 0 | 0 | 0 | 0 | 0 |
| 25° C./1 month | 0.42 | 1.38 | 1.00 | 0.56 | 0.57 | 2.10 | 7.3 |

Example 7

In accordance with the general procedure of Example 3, the RTU bivalirudin composition shown in Table 8 was prepared.

TABLE 8

| Ingredients | Quantity |
|---|---|
| Bivalirudin | 5 mg/mL |
| Sodium acetate | 0.05 M |
| Sodium hydroxide 1 M | q.s. to pH 4 |
| Water | q.s. |

The samples were stored at 25° C. for 1 month and the stability data is presented below in Table 9.

TABLE 9

| | Known Impurities (% AUC) | | | | | | Total Degradants (% AUC) |
|---|---|---|---|---|---|---|---|
| Time | Imp. 1 | Imp. 2 | Imp. 3 | Imp. 4 | Imp. 5 | Imp. 6 | |
| Initial | 0 | 0 | 0 | 0 | 0 | 0 | 0 |
| 25° C./1 month | 0 | 1.38 | 1.07 | 0.57 | 0.54 | 1.92 | 6.5 |

Example 8

In accordance with the general procedure of Example 3, the RTU bivalirudin composition shown in Table 10 was prepared.

TABLE 10

| Ingredients | Quantity |
|---|---|
| Bivalirudin | 5 mg/mL |
| L-Histidine | 0.05 M |
| Sodium acetate | 0.01 M |
| Acetic acid 1 M | q.s. to pH 4.5 |
| Water | q.s. |

The samples were stored at 25° C. for 1 month and 5° C. for 8 months and the stability data is presented below in Table 11.

TABLE 11

| | Known Impurities (% AUC) | | | | | | Total Degradants (% AUC) |
|---|---|---|---|---|---|---|---|
| Time | Imp. 1 | Imp. 2 | Imp. 3 | Imp. 4 | Imp. 5 | Imp. 6 | |
| Initial | 0 | 0 | 0.04 | 0.21 | 0.04 | 0 | 0.4 |
| 25° C./1 month | 0.74 | 2.34 | 0.97 | 1.18 | 1.14 | 2.15 | 8.8 |
| 5° C./8 months | 0.44 | 1.77 | 0.94 | 1.47 | 1.09 | 2.28 | 10.0 |

Example 9

In accordance with the general procedure of Example 3, the RTU bivalirudin composition shown in Table 12 was prepared.

TABLE 12

| Ingredients | Quantity |
|---|---|
| Bivalirudin | 5 mg/mL |
| Sodium acetate | 0.05 M |
| Lactobionic acid | 2 mg/mL |
| HES | 5% |
| Acetic acid 2 M | q.s. to pH 4.5 |
| Water | q.s. |

The samples were stored at 25° C. for 1 month and the stability data is presented below in Table 13.

TABLE 13

| | Known Impurities (% AUC) | | | | | | Total Degradants (% AUC) |
|---|---|---|---|---|---|---|---|
| Time | Imp. 1 | Imp. 2 | Imp. 3 | Imp. 4 | Imp. 5 | Imp. 6 | |
| Initial | 0 | 0 | 0 | 0.26 | 0 | 0 | 0.4 |
| 25° C./1 month | 0.80 | 2.40 | 0.91 | 1.15 | 1.13 | 0.54 | 7.6 |

Example 10

In accordance with the general procedure of Example 3, the RTU bivalirudin composition shown in Table 14 was prepared.

TABLE 14

| Ingredients | Quantity |
|---|---|
| Bivalirudin | 5 mg/mL |
| Sodium acetate | 0.05 M |
| HES | 50 mg/mL |
| Sucrose | 2 mg/mL |
| Acetic acid 2 M | q.s. to pH 4.25 |
| Water | q.s. |

The samples were stored at 25° C. for 1 month, 5° C. for 8 months, and 5° C. for 11 months. The stability data is presented below in Table 15.

TABLE 15

| | Known Impurities (% AUC) | | | | | | Total Degradants (% AUC) |
|---|---|---|---|---|---|---|---|
| Time | Imp. 1 | Imp. 2 | Imp. 3 | Imp. 4 | Imp. 5 | Imp. 6 | |
| Initial | 0 | 0 | 0 | 0.19 | 0 | 0 | 0.3 |
| 25° C./1 month | 0.59 | 1.06 | 0 | 1.11 | 1.07 | 2.08 | 9.3 |
| 5° C./8 months | 0.35 | 1.90 | 1.14 | 1.50 | 1.24 | 2.47 | 10.0 |
| 5° C./11 months | 0.10 | 1.61 | 1.00 | 1.67 | 1.13 | 3.58 | 10.6 |

Example 11

In accordance with the general procedure of Example 3, the RTU bivalirudin composition shown in Table 16 was prepared.

TABLE 16

| Ingredients | Quantity |
| --- | --- |
| Bivalirudin | 5 mg/mL |
| Sodium acetate | 0.05 M |
| Hydrochloric acid | q.s. to pH 4.5 |
| Sodium hydroxide 1 M | q.s. to pH 4.5 |
| Water | q.s. |

The samples were stored at 25° C. for 1 month and the stability data is presented below in Table 17.

TABLE 17

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | 0 | 0 | 0 | 0.28 | 0 | 0 | 0.5 |
| 25° C./1 month | 0.31 | 1.09 | 0.80 | 0.65 | 0.70 | 1.14 | 5.3 |

Example 12

In accordance with the general procedure of Example 3, the RTU bivalirudin composition shown in Table 18 was prepared.

TABLE 18

| Ingredients | Quantity |
| --- | --- |
| Bivalirudin | 5 mg/mL |
| Succinic acid | 0.05 M |
| Sodium hydroxide 1 M | q.s. to pH 4 |
| Water | q.s. |

The samples were stored at 25° C. for 1 month and the stability data is presented below in Table 19.

TABLE 19

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | 0 | 0 | 0.38 | 0.22 | 0 | 0 | 0.9 |
| 25° C./1 month | 0.19 | 0.74 | 1.37 | 0.50 | 0.26 | 1.13 | 5.4 |

Example 13

In accordance with the general procedure of Example 3, the RTU bivalirudin composition shown in Table 20 was prepared.

TABLE 20

| Ingredients | Quantity |
| --- | --- |
| Bivalirudin | 5 mg/mL |
| Succinic acid | 0.05 M |
| Sodium hydroxide 1 M | q.s. to pH 4.5 |
| Water | q.s. |

The samples were stored at 25° C. for 1 month and the stability data is presented below in Table 21.

TABLE 21

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | 0 | 0 | 0.31 | 0.63 | 0 | 0 | 1.3 |
| 25° C./1 month | 0.35 | 1.23 | 0.94 | 0.73 | 0.59 | 1.74 | 7.1 |

Example 14

In accordance with the general procedure of Example 3, the RTU bivalirudin composition shown in Table 22 was prepared.

TABLE 22

| Ingredients | Quantity |
| --- | --- |
| Bivalirudin | 5 mg/mL |
| Sodium citrate | 0.05 M |
| Hydrochloric acid | q.s. to pH 4 |
| Sodium hydroxide 1 M | q.s. to pH 4 |
| Water | q.s. |

The samples were stored at 25° C. for 1 month and the stability data is presented below in Table 23.

TABLE 23

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | 0 | 0 | 0.31 | 1.10 | 0 | 0 | 1.6 |
| 25° C./1 month | 0.19 | 0.77 | 1.55 | 0.66 | 0.46 | 2.32 | 6.8 |

Example 15

In accordance with the general procedure of Example 3, the RTU bivalirudin composition shown in Table 24 was prepared.

TABLE 24

| Ingredients | Quantity |
| --- | --- |
| Bivalirudin | 5 mg/mL |
| Lactic acid | 0.5 M |
| Sodium hydroxide 1 M | q.s. to pH 4 |
| Water | q.s. |

The samples were stored at 25° C. for 1 month and the stability data is presented below in Table 25.

TABLE 25

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | 0 | 0 | 0.24 | 0.26 | 0 | 0 | 0.7 |
| 25° C./1 month | 0.37 | 0.97 | 1.27 | 0.73 | 0.38 | 1.66 | 7.7 |

Example 16

In accordance with the general procedure of Example 3, the RTU bivalirudin composition shown in Table 26 was prepared.

TABLE 26

| Ingredients | Quantity |
|---|---|
| Bivalirudin | 5 mg/mL |
| Lactic acid | 0.5 M |
| Sodium hydroxide 1 M | q.s. to pH 4.5 |
| Water | q.s. |

The samples were stored at 25° C. for 1 month and the stability data is presented below in Table 27.

TABLE 27

| | Known Impurities (% AUC) | | | | | | |
|---|---|---|---|---|---|---|---|
| Time | Imp. 1 | Imp. 2 | Imp. 3 | Imp. 4 | Imp. 5 | Imp. 6 | Total Degradants (% AUC) |
| Initial | 0 | 0 | 0.26 | 0.62 | 0.94 | 0 | 2.0 |
| 25° C./ 1 month | 0.32 | 1.23 | 0.83 | 0.58 | 0.50 | 1.53 | 5.3 |

Example 17

In accordance with the general procedure of Example 3, the RTU bivalirudin composition shown in Table 28 was prepared.

TABLE 28

| Ingredients | Quantity |
|---|---|
| Bivalirudin | 5 mg/mL |
| Tartaric acid | 0.05 M |
| Sodium hydroxide 1 M | q.s. to pH 4 |
| Water | q.s. |

The samples were stored at 25° C. for 1 month and the stability data is presented below in Table 29.

TABLE 29

| | Known Impurities (% AUC) | | | | | | |
|---|---|---|---|---|---|---|---|
| Time | Imp. 1 | Imp. 2 | Imp. 3 | Imp. 4 | Imp. 5 | Imp. 6 | Total Degradants (% AUC) |
| Initial | 0 | 0 | 0.16 | 0.23 | 0 | 0 | 0.6 |
| 25° C./ 1 month | 0.14 | 0.67 | 1.32 | 0.54 | 0.34 | 1.80 | 5.8 |

Example 18

In accordance with the general procedure of Example 3, the RTU bivalirudin composition shown in Table 30 was prepared.

TABLE 30

| Ingredients | Quantity |
|---|---|
| Bivalirudin | 5 mg/mL |
| Tartaric acid | 0.05 M |

TABLE 30-continued

| Ingredients | Quantity |
|---|---|
| Sodium hydroxide 1 M | q.s. to pH 4.5 |
| Water | q.s. |

The samples were stored at 25° C. for 1 month and the stability data is presented below in Table 31.

TABLE 31

| | Known Impurities (% AUC) | | | | | | |
|---|---|---|---|---|---|---|---|
| Time | Imp. 1 | Imp. 2 | Imp. 3 | Imp. 4 | Imp. 5 | Imp. 6 | Total Degradants (% AUC) |
| Initial | 0 | 0 | 0.20 | 0.16 | 0 | 0 | 0.6 |
| 25° C./ 1 month | 0.24 | 1.05 | 0.57 | 0.92 | 0.79 | 0.64 | 6.1 |

Example 19

In accordance with the general procedure of Example 3, the RTU bivalirudin composition shown in Table 32 was prepared.

TABLE 32

| Ingredients | Quantity |
|---|---|
| Bivalirudin | 50 mg/mL |
| α-Lipoic acid | 25 pg/mL |
| Sucrose | 5% |
| Sodium hydroxide 1 M | q.s. to pH 4.5 |
| Water | q.s. |

The samples were stored at 25° C. for 1 month and the stability data is presented below in Table 33.

TABLE 33

| | Known Impurities (% AUC) | | | | | | |
|---|---|---|---|---|---|---|---|
| Time | Imp. 1 | Imp. 2 | Imp. 3 | Imp. 4 | Imp. 5 | Imp. 6 | Total Degradants (% AUC) |
| Initial | 0 | 0 | 0 | 0.62 | 0 | 0 | 0.9 |
| 25° C./ 1 month | 0.83 | 0.90 | 0.79 | 1.29 | 0.73 | 1.49 | 7.3 |

Example 20

In accordance with the general procedure of Example 3, the RTU bivalirudin composition shown in Table 34 was prepared.

TABLE 34

| Ingredients | Quantity |
|---|---|
| Bivalirudin | 50 mg/mL |
| Sucrose | 5% |
| HES | 10% |
| Sodium hydroxide 1 M | q.s. to pH 4.5 |
| Water | q.s. |

The samples were stored at 25° C. for 1 month and the stability data is presented below in Table 35.

TABLE 35

| Time | Known Impurities (% AUC) | | | | | | Total Degradants (% AUC) |
|---|---|---|---|---|---|---|---|
| | Imp. 1 | Imp. 2 | Imp. 3 | Imp. 4 | Imp. 5 | Imp. 6 | |
| Initial | 0 | 0 | 0.32 | 0.46 | 0 | 0.09 | 1.3 |
| 25° C./ 1 month | 0.30 | 0.95 | 0.61 | 0.68 | 1.42 | 1.06 | 6.3 |

Example 21

Alternative HPLC Method for Analysis of RTU Bivalirudin Compositions

Storage stability assessment was performed on RTU bivalirudin compositions of Examples 22-37, 39-42 by means of HPLC using the following experimental conditions Mobile Phase A: sodium acetate (50 mM, pH 6.6)

Mobile Phase B: 50% acetonitrile: 50% sodium acetate (50 mM, pH 6.6)

Column: Vydac C18, 5 μm, 250 mm×4.6 mm

Pump Mode Gradient

Flow Rate: 1.2 mL/min

Wavelength: 215 nm

Injection volume: 40 μL

Run time: 40 minutes

Column temperature: 40° C.

Gradient Program: see TABLE 36

TABLE 36

| Time | Mobile Phase B % |
|---|---|
| 0 | 10 |
| 5 | 15 |
| 30 | 35 |
| 35 | 35 |
| 35.01 | 10 |
| 40 | 10 |

Following these conditions, the following impurities were observed:

TABLE 37

| No. | Name | RRT |
|---|---|---|
| Imp. 1 | [1-11]-bivalirudin | 0.49 |
| Imp. 2 | [12-20]-bivalirudin | 0.57 |
| Imp. 3 | [3-20]-bivalirudin | 0.62 |
| Imp. 4 | $Asp^9$-bivalirudin | 0.90 |
| Imp. 5 | Co-eluting peaks that include [9-10]-cycloimido-bivalirudin | 1.07 |
| Imp. 6 | Co-eluting peaks that include [11-12]-cycloimido-bivalirudin | 1.36 |

Depending on the RTU bivalirudin composition, the relative retention time ("RRT") values can shift by about 0.1 RRT units.

Example 22

In accordance with the general procedure of Example 3, the RTU bivalirudin composition shown in Table 38 was prepared.

TABLE 38

| Ingredients | Quantity |
|---|---|
| Bivalirudin | 5 mg/mL |
| Sodium acetate | 50 mM |
| Sodium hydroxide 1 M | q.s. to pH 4.5 |
| Water | q.s. |

The samples were stored at 40° C. for 3 and 7 days and the stability data is presented below in Table 39.

TABLE 39

| Time | Known Impurities (% AUC) | | | | | | Total Degradants (% AUC) |
|---|---|---|---|---|---|---|---|
| | Imp. 1 | Imp. 2 | Imp. 3 | Imp. 4 | Imp. 5 | Imp. 6 | |
| Initial | NR | 0.32 | 0.08 | 0.47 | 0.15 | 0.06 | 1.6 |
| 40° C./3 days | NR | 1.08 | 1.61 | 0.45 | 0.92 | 2.12 | 7.7 |
| 40° C./7 days | NR | 2.08 | 3.17 | 0.61 | 1.59 | 3.72 | 14.0 |

NR = not recorded

Example 23

In accordance with the general procedure of Example 3, the RTU bivalirudin composition shown in Table 40 was prepared.

TABLE 40

| Ingredients | Quantity |
|---|---|
| Bivalirudin | 5 mg/mL |
| Sodium acetate | 50 mM |
| Glycine | 0.5% |
| Tween 80 | 0.02% |
| Sucrose | 10% |
| Glycerol | 10% |
| Sodium hydroxide 1 M | q.s. to pH 4.5 |
| Water | q.s. |

The samples were stored at 40° C. for 3 and 7 days and the stability data is presented below in Table 41.

TABLE 41

| Time | Known Impurities (% AUC) | | | | | | Total Degradants (% AUC) |
|---|---|---|---|---|---|---|---|
| | Imp. 1 | Imp. 2 | Imp. 3 | Imp. 4 | Imp. 5 | Imp. 6 | |
| Initial | NR | 0.32 | 0.08 | 0.47 | 0.14 | 0.20 | 1.9 |
| 40° C./3 days | NR | 0.99 | 1.56 | 0.43 | 0.88 | 0 | 7.1 |
| 40° C./7 days | NR | 1.82 | 3.07 | 0.59 | 1.62 | 3.81 | 14.3 |

NR = not recorded

Example 24

In accordance with the general procedure of Example 3, the RTU bivalirudin composition shown in Table 42 was prepared.

TABLE 42

| Ingredients | Quantity |
| --- | --- |
| Bivalirudin | 5 mg/mL |
| Sodium acetate | 50 mM |
| Tween 80 | 0.02% |
| Sucrose | 10% |
| Propylene Glycol | 10% |
| Sodium hydroxide 1 M | q.s. to pH 4.5 |
| Water | q.s. |

The samples were stored at 40° C. for 3 and 7 days and the stability data is presented below in Table 43.

TABLE 43

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | NR | 0.32 | 0.08 | 0.45 | 0.13 | 0.08 | 1.5 |
| 40° C./3 days | NR | 0.92 | 1.76 | 0.44 | 0.86 | 1.76 | 7.1 |
| 40° C./7 days | NR | 1.73 | 3.44 | 0.58 | 1.60 | 3.52 | 13.9 |

NR = not recorded

Example 25

In accordance with the general procedure of Example 3, the RTU bivalirudin composition shown in Table 44 was prepared.

TABLE 44

| Ingredients | Quantity |
| --- | --- |
| Bivalirudin | 5 mg/mL |
| Sodium acetate | 50 mM |
| Glycine | 0.5% |
| Tween 80 | 0.02% |
| Propylene glycol | 10% |
| Sodium hydroxide 1 M | q.s. to pH 4.5 |
| Water | q.s. |

The samples were stored at 40° C. for 3 and 7 days and the stability data is presented below in Table 45.

TABLE 45

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | NR | 0.35 | 0.10 | 0.45 | 0.13 | 0.10 | 1.6 |
| 40° C./3 days | NR | 0.98 | 1.42 | 0.46 | 1.00 | 0.00 | 7.0 |
| 40° C./7 days | NR | 1.79 | 2.79 | 0.65 | 1.74 | 3.45 | 13.0 |

NR = not recorded

Example 26

In accordance with the general procedure of Example 3, the RTU bivalirudin composition shown in Table 46 was prepared.

TABLE 46

| Ingredients | Quantity |
| --- | --- |
| Bivalirudin | 5 mg/mL |
| Sodium acetate | 50 mM |
| Glycine | 0.5% |
| Glycerol | 10% |
| Propylene glycol | 10% |
| Sodium hydroxide 1 M | q.s. to pH 4.5 |
| Water | q.s. |

The samples were stored at 40° C. for 3 and 7 days and the stability data is presented below in Table 47.

TABLE 47

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | NR | 0.34 | 0.08 | 0.48 | 0.13 | 0.08 | 1.6 |
| 40° C./3 days | NR | 1.00 | 1.68 | 0.42 | 0.82 | 0.00 | 7.5 |
| 40° C./7 days | NR | 1.95 | 3.32 | 0.49 | 1.44 | 3.88 | 14.3 |

NR = not recorded

Example 27

In accordance with the general procedure of Example 3, the RTU bivalirudin composition shown in Table 48 was prepared.

TABLE 48

| Ingredients | Quantity |
| --- | --- |
| Bivalirudin | 5 mg/mL |
| Sodium acetate | 50 mM |
| Tween 80 | 0.02% |
| Glycerol | 10% |
| Magnesium chloride | 50 mM |
| Sodium hydroxide 1 M | q.s. to pH 4.5 |
| Water | q.s. |

The samples were stored at 40° C. for 3 and 7 days and the stability data is presented below in Table 49.

TABLE 49

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | NR | 0.32 | 0.08 | 0.47 | 0.14 | 0.09 | 1.6 |
| 40° C./3 days | NR | 0.99 | 1.40 | 0.51 | 1.07 | 0.00 | 7.3 |
| 40° C./7 days | NR | 1.61 | 2.74 | 0.80 | 1.90 | 3.09 | 13.0 |

NR = not recorded

Example 28

In accordance with the general procedure of Example 3, the RTU bivalirudin composition shown in Table 50 was prepared.

TABLE 50

| Ingredients | Quantity |
| --- | --- |
| Bivalirudin | 5 mg/mL |
| Sodium acetate | 50 mM |
| Sucrose | 10% |
| Glycerol | 10% |
| Magnesium chloride | 50 mM |
| Propylene glycol | 10% |
| Sodium hydroxide 1 M | q.s. to pH 4.5 |
| Water | q.s. |

The samples were stored at 40° C. for 3 and 7 days and the stability data is presented below in Table 51.

TABLE 51

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | NR | 0.32 | 0.09 | 0.47 | 0.13 | 0.07 | 1.6 |
| 40° C./3 days | NR | 0.88 | 1.25 | 0.43 | 0.83 | 0.00 | 6.5 |
| 40° C./7 days | NR | 1.59 | 2.47 | 0.53 | 1.61 | 3.48 | 12.7 |

NR = not recorded

Example 29

In accordance with the general procedure of Example 3, the RTU bivalirudin composition shown in Table 52 was prepared.

TABLE 52

| Ingredients | Quantity |
| --- | --- |
| Bivalirudin | 5.0 mg/mL |
| PEG 400 | 10% |
| Sodium hydroxide 1 M | q.s. to pH 4.5 |
| Water | q.s. |

The samples were stored at 40° C. for 3 days and the stability data is presented below in Table 53.

TABLE 53

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | 0 | 0 | 0 | 0.55 | 0.17 | 0.05 | 1.7 |
| 40° C./3 days | 1.46 | 0 | 0.53 | 0.46 | 0.81 | 2.04 | 7.4 |

Example 30

In accordance with the general procedure of Example 3, the RTU bivalirudin composition shown in Table 54 was prepared.

TABLE 54

| Ingredients | Quantity |
| --- | --- |
| Bivalirudin | 5 mg/mL |
| PEG 400 | 10% |
| Sorbitol | 10% |
| Calcium chloride | 25 mM |
| Sodium hydroxide 1 M | q.s. to pH 4.5 |
| Water | q.s. |

The samples were stored at 40° C. for 3 days and the stability data is presented below in Table 55.

TABLE 55

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | 0.04 | 0 | 0 | 0.53 | 0.17 | 0.05 | 2.0 |
| 40° C./3 days | 1.05 | 0 | 0.36 | 0.48 | 0.90 | 1.69 | 6.5 |

Example 31

In accordance with the general procedure of Example 3, the RTU bivalirudin composition shown in Table 56 was prepared.

TABLE 56

| Ingredients | Quantity |
| --- | --- |
| Bivalirudin | 5.0 mg/mL |
| PEG 400 | 20% |
| Citric acid | 50 mM |
| Sorbitol | 20% |
| Calcium chloride | 50 mM |
| Poloxamer | 0.6% |
| Sodium hydroxide 1 M | q.s. to pH 4.5 |
| Water | q.s. |

The samples were stored at 40° C. for 3 days and the stability data is presented below in Table 57.

TABLE 57

| | Known Impurities (% AUC) | | | | | | Total Degradants (% AUC) |
|---|---|---|---|---|---|---|---|
| Time | Imp. 1 | Imp. 2 | Imp. 3 | Imp. 4 | Imp. 5 | Imp. 6 | |
| Initial | 0.06 | 0 | 0 | 0.49 | 0.16 | 0.07 | 1.9 |
| 40° C./3 days | 1.04 | 0 | 0.24 | 0.41 | 0.65 | 1.61 | 7.5 |

Example 32

In accordance with the general procedure of Example 3, the RTU bivalirudin composition shown in Table 58 was prepared.

TABLE 58

| Ingredients | Quantity |
|---|---|
| Bivalirudin | 5 mg/mL |
| Sorbitol | 15% |
| Magnesium chloride | 50 mM |
| Sodium hydroxide 1 M | q.s. to pH 4 |
| Water | q.s. |

The samples were stored at 25° C. for 1 month and at 5° C. for 6 months and the stability data is presented below in Table 59.

TABLE 59

| | Known Impurities (% AUC) | | | | | | Total Degradants (% AUC) |
|---|---|---|---|---|---|---|---|
| Time | Imp. 1 | Imp. 2 | Imp. 3 | Imp. 4 | Imp. 5 | Imp. 6 | |
| Initial | 0.03 | 0.05 | 0 | 0.51 | 0 | 0 | 1.5 |
| 25° C./1 month | 0.41 | 1.05 | 0.45 | 0.33 | 0.29 | 1.42 | 6.6 |
| 5° C./6 months | 0.54 | 0.62 | 0.18 | 0.32 | 0.33 | 0.63 | 4.2 |

NR = not recorded

Example 33

In accordance with the general procedure of Example 3, the RTU bivalirudin composition shown in Table 60 was prepared.

TABLE 60

| Ingredients | Quantity |
|---|---|
| Bivalirudin | 5 mg/mL |
| Sorbitol | 15% |
| Propylene glycol | 10% |
| Sodium hydroxide 1 M | q.s. to pH 4.5 |
| Water | q.s. |

The samples were stored at 25° C. for 1 month and at 5° C. for 6 months and the stability data is presented below in Table 61.

TABLE 61

| | Known Impurities (% AUC) | | | | | | Total Degradants (% AUC) |
|---|---|---|---|---|---|---|---|
| Time | Imp. 1 | Imp. 2 | Imp. 3 | Imp. 4 | Imp. 5 | Imp. 6 | |
| Initial | 0.01 | 0.09 | 0.04 | 0.15 | 0 | NR | 1.6 |
| 25° C./1 month | 0.24 | 0.85 | 0.78 | 0.63 | 0.38 | 1.72 | 6.3 |
| 5° C./6 months | 0.60 | 0.65 | 0.28 | 0.35 | 0.30 | 0.66 | 3.6 |

NR = not recorded

Example 34

In accordance with the general procedure of Example 3, the RTU bivalirudin composition shown in Table 62 was prepared.

TABLE 62

| Ingredients | Quantity |
|---|---|
| Bivalirudin | 5 mg/mL |
| Sorbitol | 15% |
| Propylene glycol | 10% |
| Sodium hydroxide 1 M | q.s. to pH 4 |
| Water | q.s. |

The samples were stored at 25° C. for 1 month and at 5° C. for 6 months and the stability data is presented below in Table 63.

TABLE 63

| | Known Impurities (% AUC) | | | | | | Total Degradants (% AUC) |
|---|---|---|---|---|---|---|---|
| Time | Imp. 1 | Imp. 2 | Imp. 3 | Imp. 4 | Imp. 5 | Imp. 6 | |
| Initial | 0.03 | 0.04 | 0 | 0.18 | 0.09 | NR | 1.9 |
| 25° C./1 month | 0.43 | 1.14 | 0.52 | 0.50 | 0.52 | 1.53 | 7.8 |
| 5° C./6 months | 0.61 | 0.68 | 0.17 | 0.21 | 0.15 | 0.57 | 4.1 |

NR = not recorded

Example 35

In accordance with the general procedure of Example 3, the RTU bivalirudin composition shown in Table 64 was prepared.

TABLE 64

| Ingredients | Quantity |
|---|---|
| Bivalirudin | 5 mg/mL |
| Propylene glycol | 10% |
| Sodium hydroxide 1 M | q.s. to pH 4 |
| Water | q.s. |

The samples were stored at 25° C. for 1 month and at 5° C. for 6 months and the stability data is presented below in Table 65.

TABLE 65

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | 0.03 | 0.06 | 0 | 0.04 | 0 | NR | 1.8 |
| 25° C./1 month | 0.41 | 1.14 | 0.63 | 0.46 | 0 | 1.66 | 5.9 |
| 5° C./6 months | 0.64 | 0.75 | 0.15 | 0.29 | 0.28 | 0.69 | 3.8 |

NR = not recorded

Example 36

In accordance with the general procedure of Example 3, the RTU bivalirudin composition shown in Table 66 was prepared.

TABLE 66

| Ingredients | Quantity |
| --- | --- |
| Bivalirudin | 5 mg/mL |
| PEG 400 | 20% |
| Propylene glycol | 10% |
| Sodium hydroxide 1 M | q.s. to pH 4.5 |
| Water | q.s. |

The samples were stored at 25° C. for 1 month and at 5° C. for 6 months and the stability data is presented below in Table 67.

TABLE 67

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | 0.23 | 0 | 0 | 0.13 | 0 | NR | 1.5 |
| 25° C./1 month | 0.16 | 0.70 | 0.18 | 0.58 | 0.11 | 1.47 | 5.3 |
| 5° C./6 months | 0.52 | 0.60 | 0.24 | 0.36 | 0.24 | 0.74 | 3.9 |

NR = not recorded

Example 37

In accordance with the general procedure of Example 3, the RTU bivalirudin composition shown in Table 68 was prepared.

TABLE 68

| Ingredients | Quantity |
| --- | --- |
| Bivalirudin | 5 mg/mL |
| Sorbitol | 15% |
| PEG 400 | 20% |
| Sodium hydroxide 1 M | q.s. to pH 5 |
| Water | q.s. |

The samples were stored at 25° C. for 1 month and 5° C. for 6 months and the stability data is presented below in Table 69.

TABLE 69

| Time | Known Impurities (% AUC) | | | | | | Total Degradants (% AUC) |
| --- | --- | --- | --- | --- | --- | --- | --- |
| | Imp. 1 | Imp. 2 | Imp. 3 | Imp. 4 | Imp. 5 | Imp. 6 | |
| Initial | 0.26 | 0.18 | 0 | 0.14 | 0 | NR | 1.8 |
| 25° C./1 month | 0 | 0.78 | 0 | 0.63 | 0.19 | 1.66 | 5.1 |
| 5° C./6 months | 0.56 | 0.68 | 0.29 | 0.36 | 0.36 | 0.76 | 4.0 |

NR = not recorded

Example 38

General Procedure for the Preparation of 1 L RTU Bivalirudin Compositions

A 2 M acetic acid solution was prepared by diluting 23.03 mL of acetic acid with water in a 200 mL volumetric flask. A 1 N NaOH solution was prepared by dissolving 8 g of NaOH with water in a 200 mL volumetric flask. A 0.05 M sodium acetate solution was prepared by dissolving 13.68 g of sodium acetate trihydrate in 1600 mL of water and adjusting the pH to 4.25 by the addition of 2 M acetic acid solution (approximately 100 mL).

Bivalirudin (5.85 g) was slowly added with stirring to one part of the sodium acetate solution while maintaining the pH between about 4.15 and 4.35. In the event the drug substance stuck to the glass beaker, 1 N NaOH solution was added (approximately 15 mL) until the pH was raised to about 4.35. After all the drug substance was added, the pH of the drug solution was adjusted to 4.25 with 2 M acetic acid (approximately 1.7 mL).

The solution was filtered through a 0.22 μm sterilized filter and purged with nitrogen for about 10 min. The filtered drug solution was transferred into 50 mL piggyback vials and 5 mL glass vials ($SO_2$ treated, USP Type I flint glass vials). After additional nitrogen purging (approximately 30 seconds for each vial), the vials were closed with stoppers and crimped.

Example 39

In accordance with the general procedure of Example 38, the RTU bivalirudin composition shown in Table 70 was prepared.

TABLE 70

| Ingredients | Quantity |
| --- | --- |
| Bivalirudin | 5 mg/mL |
| Sodium acetate | 0.05 M |
| Acetic acid | 2 M |
| Sodium hydroxide 1 M | q.s. to pH 4.25 |
| Water | q.s. |

The samples were stored at 5° C. for 3, 6, 9 and 12 months and at 25° C. for 1 month and the stability data is presented below in Table 71.

TABLE 71

| Time | Imp. 1 | Imp. 2 | Imp. 3 | Imp. 4 | Imp. 5 | Imp. 6 | Total Degradants (% AUC) |
|---|---|---|---|---|---|---|---|
| | Known Impurities (% AUC) | | | | | | |
| Initial | 0.09 | 0.26 | 0.15 | 0.27 | 0.12 | 0.18 | 1.2 |
| 5° C./2 months | 0.21 | 0.47 | 0.42 | 0.30 | 0.35 | 0.84 | 2.6 |
| 5° C./6 months | 0.13 | 0.66 | 0.72 | 0.28 | 0.51 | 1.44 | 4.2 |
| 5° C./9 months | 0.11 | 0.87 | 1.44 | 0.33 | 1.40 | 2.00 | 6.4 |
| 5° C./12 months | 0.24 | 1.18 | 1.87 | 0.49 | 1.04 | 2.73 | 8.5 |
| 25° C./1 month | 0.44 | 1.19 | 2.32 | 0.51 | 1.08 | 2.60 | 9.0 |

Example 40

In accordance with the general procedure of Example 38, the RTU bivalirudin composition shown in Table 72 was prepared.

TABLE 72

| Ingredients | Quantity |
|---|---|
| Bivalirudin | 5 mg/mL |
| Sodium acetate | 0.05 M |
| Acetic acid | 2 M |
| Sodium hydroxide 1 M | q.s. to pH 4.25 |
| Sodium chloride | 9 mg/mL |
| Water | q.s. |

The samples were stored at 5° C. for 2, 6, 9 and 12 months and at 25° C. for 1 month and the stability data is presented below in Table 73.

TABLE 73

| Time | Imp. 1 | Imp. 2 | Imp. 3 | Imp. 4 | Imp. 5 | Imp. 6 | Total Degradants (% AUC) |
|---|---|---|---|---|---|---|---|
| | Known Impurities (% AUC) | | | | | | |
| Initial | 0.09 | 0.28 | 0.09 | 0.32 | 0.11 | 0.11 | 1.2 |
| 5° C./2 months | 0.11 | 0.40 | 0.24 | 0.28 | 0.26 | 0.64 | 1.9 |
| 5° C./6 months | 0.17 | 0.67 | 0.58 | 0.31 | 0.55 | 1.46 | 4.2 |
| 5° C./9 months | 0.10 | 0.85 | 0.94 | 0.28 | 1.39 | 1.74 | 5.6 |
| 5° C./12 months | 0.18 | 1.14 | 1.25 | 0.43 | 0.93 | 2.51 | 7.4 |
| 25° C./1 month | 0.63 | 1.33 | 1.91 | 0.51 | 1.16 | 2.74 | 8.6 |

Example 41

In accordance with the general procedure of Example 38, the RTU bivalirudin composition shown in Table 74 was prepared.

TABLE 74

| Ingredients | Quantity |
|---|---|
| Bivalirudin | 5 mg/mL |
| Sodium acetate | 0.05 M |
| Acetic acid 2 M | q.s. to pH 4.25 |
| Methyl paraben | 0.1% |
| Sodium chloride | 9 mg/mL |
| Water | q.s. |

The samples were stored at 5° C. for 2, 6, 9 and 12 months and at 25° C. for 1 month and the stability data is presented below in Table 75.

TABLE 75

| Time | Imp. 1 | Imp. 2 | Imp. 3 | Imp. 4 | Imp. 5 | Imp. 6 | Total Degradants (% AUC) |
|---|---|---|---|---|---|---|---|
| | Known Impurities (% AUC) | | | | | | |
| Initial | 0.09 | 0.26 | 0.08 | 0.35 | 0.11 | 0 | 1.0 |
| 5° C./2 months | 0 | 0.39 | 0.22 | 0.26 | 0.33 | 0.62 | 2.1 |
| 5° C./6 months | 0.06 | 0.66 | 0.52 | 0.28 | 0.93 | 1.51 | 4.4 |
| 5° C./9 months | 0 | 0 | 0 | 0.37 | 1.36 | 2.14 | 6.1 |
| 5° C./12 months | 0.17 | 1.32 | 1.48 | 0.47 | 1.02 | 2.81 | 8.2 |
| 25° C./1 month | 0.79 | 1.32 | 1.94 | 0.52 | 1.22 | 2.88 | 9.1 |

Example 42

In accordance with the general procedure of Example 38, the RTU bivalirudin composition shown in Table 76 was prepared.

TABLE 76

| Ingredients | Quantity |
|---|---|
| Bivalirudin | 5 mg/mL |
| Sodium acetate | 0.05 M |
| L-Histidine | 1 mg/mL |
| L-Methionine | 1 mg/mL |
| Acetic acid 2 M | q.s. to pH 4.25 |
| Sodium chloride | 9 mg/mL |
| Water | q.s. |

The samples were stored at 5° C. for 2, 6, 9 and 12 months and at 25° C. for 1 month and the stability data is presented below in Table 77.

TABLE 77

| Time | Imp. 1 | Imp. 2 | Imp. 3 | Imp. 4 | Imp. 5 | Imp. 6 | Total Degradants (% AUC) |
|---|---|---|---|---|---|---|---|
| | Known Impurities (% AUC) | | | | | | |
| Initial | 0 | 0.20 | 0.07 | 0.30 | 0.10 | 0 | 0.7 |
| 5° C./2 months | 0.10 | 0.38 | 0.19 | 0.26 | 0.29 | 0.59 | 2.0 |
| 5° C./6 months | 0.10 | 0.67 | 0.60 | 0.26 | 1.02 | 1.47 | 4.5 |
| 5° C./9 months | 0.13 | 0.94 | 1.07 | 0.26 | 1.38 | 2.05 | 5.8 |
| 5° C./12 months | 0.52 | 1.26 | 1.44 | 0.46 | 0.97 | 2.70 | 8.0 |
| 25° C./1 month | 0.48 | 1.40 | 1.91 | 0.50 | 1.17 | 2.71 | 8.7 |

Example 43

Prediction of Shelf-Life for Selected Formulations at about 5° C. Based on % Bivalirudin The shelf life of RTU bivalirudin compositions at about 5° C. was predicted using an Arrhenius plot to project the amount of time until the bivalirudin content reached 90%. In addition, for some compositions shelf life was predicted based on the stability data at 5° C. for 6 months.

TABLE 78

| Example # | Bivalirudin Content (>90%) |
|---|---|
| 32 | ~16 months |
| 33 | ~24 months |
| 34 | ~17 months |
| 35 | ~19 months |
| 36 | ~17 months |
| 37 | ~17 months |

TABLE 78-continued

| Example # | Bivalirudin Content (>90%) |
|---|---|
| 39 | ~18 months |
| 40 | ~19 months |

The data from Table 78 suggests that a shelf life of greater than 16 months may be attainable when the RTU bivalirudin compositions are stored at about 5° C.

What is claimed is:

1. An aqueous, injectable composition that has not been reconstituted from a lyophilizate, comprising:
   (i) bivalirudin (SEQ ID NO: 1), or salts thereof, at a concentration of about 1 mg/mL to about 10 mg/mL;
   (ii) one or more pharmaceutically acceptable stabilizing agents, wherein at least one of the stabilizing agents is a buffering agent having a pKa of about 2.5 to about 6.5;
   (iii) a pH of about 4 to less than 5; and
   (iv) total impurities in an amount less than about 1.5% area-under-the-curve ("AUC") as determined by high performance liquid chromatography ("HPLC") at a wavelength of 215 nm after storage at 25° C. for 1 month.

2. The composition of claim 1, wherein the bivalirudin is at a concentration of about 5 mg/mL.

3. The composition of claim 1, wherein the bivalirudin is at a concentration of about 10 mg/mL.

4. The composition of claim 1, wherein the buffering agent is selected from a group consisting of acetate, tartrate, ascorbate, lactobionate, gentisate, succinate, lactate, α-lipoic acid, and any combination thereof.

5. The composition of claim 4, wherein the buffering agent is acetate.

6. The composition of claim 1, wherein the buffering agent has a pKa of about 3.5 to about 5.

7. The composition of claim 6, wherein the buffering agent has a pKa of about 4.2 to about 4.5.

8. The composition of claim 1, wherein the pH is obtained by a pH-adjusting agent.

9. The composition of claim 8, wherein the pH-adjusting agent comprises an acid or base.

10. The composition of claim 9, wherein the pH-adjusting agent comprises acetic acid or sodium hydroxide.

11. The composition of claim 1, wherein the pH is about 4.2 to about 4.5.

12. The composition of claim 1, wherein the total impurities are less than about 10% AUC as determined by HPLC after storage at 25° C. for 1 month.

13. The composition of claim 1, comprising at least one preservative.

14. The composition of claim 13, wherein the preservative is methyl-paraben.

15. The composition of claim 1, comprising at least one antioxidant.

16. The composition of claim 15, wherein the antioxidant is selected from a group consisting of histidine, methionine, and any combination thereof.

17. The composition of claim 1, comprising at least one inorganic salt.

18. The composition of claim 17, wherein the inorganic salt is sodium chloride.

19. An aqueous, injectable composition that has not been reconstituted from a lyophilizate, comprising:
   (i) bivalirudin (SEQ ID NO: 1), or salts thereof, at a concentration of about 1 mg/mL to about 10 mg/mL;
   (ii) one or more pharmaceutically acceptable stabilizing agents, wherein at least one of the stabilizing agents is a buffering agent having a pKa of about 2.5 to about 6.5;
   (iii) a pH of about 4 to less than 5; and
   (iv) total impurities in an amount less than about 12% area-under-the-curve ("AUC") as determined by high performance liquid chromatography ("HPLC") at a wavelength of 215 nm after storage at about 2° C. to about 8° C. for 12 months.

20. The composition of claim 19, wherein the bivalirudin is at a concentration of about 5 mg/mL.

21. The composition of claim 19, wherein the bivalirudin is at a concentration of about 10 mg/mL.

22. The composition of claim 19, wherein the buffering agent is selected from a group consisting of acetate, tartrate, ascorbate, lactobionate, gentisate, succinate, lactate, α-lipoic acid, and any combination thereof.

23. The composition of claim 22, wherein the buffering agent is acetate.

24. The composition of claim 19, wherein the buffering agent has a pKa of about 3.5 to about 5.

25. The composition of claim 24, wherein the buffering agent has a pKa of about 4.2 to about 4.5.

26. The composition of claim 19, wherein the pH is obtained by a pH-adjusting agent.

27. The composition of claim 26, wherein the pH-adjusting agent comprises an acid or base.

28. The composition of claim 27, wherein the pH-adjusting agent comprises acetic acid or sodium hydroxide.

29. The composition of claim 19, wherein the pH is about 4.2 to about 4.5.

30. The composition of claim 19, wherein the total impurities are less than about 10% AUC as determined by HPLC after storage at about 2° C. to about 8° C. for 12 months.

31. The composition of claim 19, comprising at least one preservative.

32. The composition of claim 31, wherein the preservative is methyl-paraben.

33. The composition of claim 19, comprising at least one antioxidant.

34. The composition of claim 33, wherein the antioxidant is selected from a group consisting of histidine, methionine, and any combination thereof.

35. The composition of claim 19, comprising at least one inorganic salt.

36. The composition of claim 35, wherein the inorganic salt is sodium chloride.

37. An aqueous, injectable composition that has not been reconstituted from a lyophilizate, comprising:
   (i) bivalirudin (SEQ ID NO: 1), or salts thereof, at a concentration of about 1 mg/mL to about 10 mg/mL;
   (ii) one or more pharmaceutically acceptable stabilizing agents, wherein at least one of the stabilizing agents is selected from a group consisting of (a) polymers, and (b) sugars or polyols;
   (iii) a pH of about 4 to less than 5 as obtained by a pH-adjusting agent; and
   (iv) total impurities present in an amount less than about 15% area-under-the-curve ("AUC") as determined by high performance liquid chromatography ("HPLC") at a wavelength of 215 nm after storage at 25° C. for 1 month.

38. The composition of claim 37, wherein the bivalirudin is at a concentration of about 5 mg/mL.

39. The composition of claim 37, wherein the bivalirudin is at a concentration of about 10 mg/mL.

40. The composition of claim 37, wherein the polymers are selected from a group consisting of polyethylene glycol, poloxamer, polysorbates, hydroxyethyl starch, polyvinylpyrrolidone, and any combination thereof.

41. The composition of claim 37, wherein the sugars or polyols are selected from a group consisting of sucrose, dextrose, dextrin, propylene glycol, sorbitol, glycerol, and any combination thereof.

42. The composition of claim 37, wherein the pH-adjusting agent is selected from a group consisting of an acid, base, and buffering agent.

43. The composition of claim 42, wherein the pH-adjusting agent comprises acetic acid or sodium hydroxide.

44. The composition of claim 37, wherein the pH is about 4.2 to about 4.5.

45. The composition of claim 37, wherein the total impurities are less than about 10% AUC as determined by HPLC after storage at 25° C. for 1 month.

46. The composition of claim 37, comprising at least one preservative.

47. The composition of claim 46, wherein the preservative is methyl-paraben.

48. The composition of claim 37, comprising at least one antioxidant.

49. The composition of claim 48, wherein the antioxidant is selected from a group consisting of histidine, methionine, and any combination thereof.

50. The composition of claim 37, comprising at least one inorganic salt.

51. The composition of claim 50, wherein the inorganic salt is sodium chloride.

52. An aqueous, injectable composition that has not been reconstituted from a lyophilizate, comprising:
   (i) bivalirudin in an amount of about 5 mg/mL;
   (ii) a buffering agent having a pKa of about 2.5 to about 6.5, wherein the buffering agent is acetate;
   (iii) a pH of about 4.2; and
   (iv) total impurities in an amount less than about 15% area-under-the-curve ("AUC") as determined by high performance liquid chromatography ("HPLC") at a wavelength of 215 nm after storage at 25° C. for 1 month.

53. An aqueous, injectable composition that has not been reconstituted from a lyophilizate, comprising:
   (v) bivalirudin, or salts thereof, in an amount of about 5 mg/mL;
   (vi) a buffering agent having a pKa of about 2.5 to about 6.5, wherein the buffering agent is acetate;
   (vii) sodium chloride;
   (viii) a pH of about 4.2; and
   (ix) total impurities in an amount less than about 15% area-under-the-curve ("AUC") as determined by high performance liquid chromatography ("HPLC") at a wavelength of 215 nm after storage at 25° C. for 1 month.

* * * * *

UNITED STATES PATENT AND TRADEMARK OFFICE
CERTIFICATE OF CORRECTION

PATENT NO.         : 7,803,762 B1
APPLICATION NO.    : 12/545036
DATED              : September 28, 2010
INVENTOR(S)        : Nagesh Palepu et al.

Page 1 of 1

It is certified that error appears in the above-identified patent and that said Letters Patent is hereby corrected as shown below:

Claim 1, line 9 (column 37, line 39), should be canceled and the following should be inserted:

--(iv) total impurities in an amount less than about 15%--

Signed and Sealed this
Second Day of October, 2012

David J. Kappos
*Director of the United States Patent and Trademark Office*